(12) United States Patent
Calderon et al.

(10) Patent No.: US 9,724,523 B2
(45) Date of Patent: Aug. 8, 2017

(54) EPG LEADED INTERFACE

(71) Applicant: THE ALFRED E. MANN FOUNDATION FOR SCIENTIFIC RESEARCH, Santa Clara, CA (US)

(72) Inventors: Joseph L. Calderon, Culver City, CA (US); Edward Hillery, Valencia, CA (US); Joseph Lockhart, Valencia, CA (US)

(73) Assignee: ALFRED E. MANN FOUNDATION FOR SCIENTIFIC RESEARCH, Santa Clarita, CA (US)

( * ) Notice: Subject to any disclaimer, the term of this patent is extended or adjusted under 35 U.S.C. 154(b) by 0 days.

(21) Appl. No.: 14/940,090

(22) Filed: Nov. 12, 2015

(65) Prior Publication Data

US 2016/0136435 A1 May 19, 2016

Related U.S. Application Data

(60) Provisional application No. 62/079,193, filed on Nov. 13, 2014.

(51) Int. Cl.
*H01R 39/00* (2006.01)
*A61N 1/375* (2006.01)
*A61N 1/05* (2006.01)
*A61N 1/36* (2006.01)

(52) U.S. Cl.
CPC ............. *A61N 1/3752* (2013.01); *A61N 1/05* (2013.01); *A61N 1/375* (2013.01); *A61N 1/0502* (2013.01); *A61N 1/0595* (2013.01); *A61N 1/36017* (2013.01)

(58) Field of Classification Search
CPC .............. A61N 1/3752; A61N 1/0595; A61N 1/36017; A61N 1/05; A61N 1/375; A61N 1/0502; H01R 13/6658; H01R 13/719; H01R 23/005
See application file for complete search history.

(56) References Cited

U.S. PATENT DOCUMENTS

| | | | |
|---|---|---|---|
| 4,245,642 A | 1/1981 | Skubitz et al. | |
| 5,560,358 A | 10/1996 | Arnold et al. | |
| 6,154,678 A | 11/2000 | Lauro | |
| 6,343,233 B1 | 1/2002 | Werner et al. | |
| 6,671,534 B2 | 12/2003 | Putz | |
| 6,741,892 B1 | 5/2004 | Meadows et al. | |
| 7,539,542 B1 * | 5/2009 | Malinowski | A61N 1/3752 439/909 |
| 7,548,788 B2 | 6/2009 | Chinn et al. | |

(Continued)

OTHER PUBLICATIONS

International Search Report and Written Opinion, PCT Application PCT/US15/60483, Feb. 22, 2016.

*Primary Examiner* — Jean F Duverne
(74) *Attorney, Agent, or Firm* — Lewis Roca Rothgerber Christie LLP

(57) ABSTRACT

An interface for coupling with a percutaneously implantable lead is described. The interface includes a rotation based system to engage the terminal connector of the lead. The interface includes a brake which retains the lead in the lead port through friction, but allows the lead to exit the lead port if sufficient force is applied. The interface can be coupled with the lead without removing a stylet or stiffening wire from the lead.

37 Claims, 17 Drawing Sheets

(56) References Cited

U.S. PATENT DOCUMENTS

| | | | |
|---|---|---|---|
| 7,860,570 B2 * | 12/2010 | Whitehurst | A61N 1/37205 607/118 |
| 8,046,074 B2 * | 10/2011 | Barker | A61N 1/05 607/37 |
| 8,342,887 B2 | 1/2013 | Gleason et al. | |
| 8,401,670 B2 | 3/2013 | Mehdizadeh et al. | |
| 8,548,601 B2 | 10/2013 | Chinn | |
| 8,996,128 B2 | 3/2015 | Parker et al. | |
| 9,101,775 B2 | 8/2015 | Barker | |
| 2004/0230268 A1 | 11/2004 | Huff et al. | |
| 2005/0202427 A1 | 9/2005 | Soufla | |
| 2010/0048062 A1 | 2/2010 | Cappa et al. | |
| 2010/0070012 A1 | 3/2010 | Chinn et al. | |
| 2011/0098795 A1 | 4/2011 | Mehdizadeh et al. | |
| 2011/0257503 A1 | 10/2011 | Mehdizadeh et al. | |

\* cited by examiner

EPG LEADED INTERFACE

CROSS REFERENCE TO RELATED APPLICATIONS

The present application claims benefit under 35 U.S.C. §119(e) to U.S. Provisional Application Ser. No. 62/079,193, filed on Nov. 13, 2014 which is incorporated herein by reference in its entirety.

BACKGROUND

Various medical devices have been developed which apply electrical stimulation to the tissue of a patient in order to elicit muscle movement or treat a medical condition, including implantable pulse generators and microstimulators. Other medical devices have been developed which monitor electrical characteristics inside the body, such as impedance across a given area, electroneurogram signals, electrocardiogram signals, or electromyogram signals. These devices often use fully implanted or percutaneously implanted medical leads to provide stimulation or sensing at sites throughout a patient's body.

When implanting a medical lead percutaneously, the distal end of the lead is implanted in tissue at the therapy site and the proximal end protrudes through the skin and outside the body. The proximal end of the lead can be connected to an external device, such as an external pulse generator. The external device typically has a connector or lead interface (hereinafter 'interface') capable of coupling, temporarily, to the terminal connector of the lead.

An external device may be used during the implantation procedure for a fully implanted lead and implanted medical device. Before the proximal portion of the lead is connected to the implantable medical device and implanted, it can is connected to the external device to determine whether the distal end of the lead is in a position to deliver stimulation to the correct site or to sense the desired signal. This process may involve connecting and disconnecting the interface several times. This can lead to problems when an interface cannot be securely attached and removed, multiple times, quickly and easily.

Some lead implantation procedures use a stiffening wire or a steering stylet. The stiffening wire or steering stylet extends through a lumen running the length of the lead and protrudes from the proximal end of the terminal connector. If an interface cannot accommodate the portion protruding from the lead, then the wire or stylet must be completely removed from the lead. If, upon testing, it is discovered that the lead needs to be moved, the wire or stylet must be reinserted into the lead.

The external device may additionally or alternatively be carried with the patient during a trial period and used to determine whether the therapy will be efficacious before the more onerous and expensive step of connecting to and implanting an implantable medical device is taken, or used during a temporary treatment in which a fully implanted medical device is not desired. Under these circumstances, the lead extends percutaneously to the interface, and the patient keeps the interface and the external device on their person for the duration of the test period, which may be one or more weeks. During this period, the patient goes about their life, exposing the lead, interface, and external device to unpredictable circumstances. If the mechanism engaging the lead in the interface inadvertently moves from the closed position to the open position during this trial period, the connection between the external device and the lead can be lost and the lead can become removed from the interface at unwanted times. On the other hand, if the external device or interface fall or are pulled on, or if the lead is caught on something, the pressure applied to the lead can cause discomfort, pain, or in extreme situations could dislodge the distal end of the lead from the implantation site. Further, a large interface can grow cumbersome or embarrassing to a patient who has to keep the device on their person for extended periods.

Conventional interfaces do not address all the foregoing considerations. Accordingly, there remains a need for improved techniques and systems for temporarily connecting percutaneously implantable medical leads to external devices.

SUMMARY

One aspect of the present disclosure relates to an interface for coupling to a lead. The lead has a terminal connector at the proximal end of the lead, the terminal connector having at least one terminal contact. The interface comprises a housing, a lead, and at least one contact. The housing comprises a lead port. The lead port is configured to receive the terminal connector. The lead engaging mechanism is variable between an open position and a closed position, and the at least one contact moves responsive to the lead engaging mechanism. The at least one contact is in a position to be in electrical communication with the at least one terminal contact when the lead engaging mechanism is in the closed position and the terminal connector is in the lead port.

In some embodiments, the interface comprises a brake which moves responsive to the lead engaging mechanism. The brake is in a first position where it is frictionally coupled with the lead when the terminal connector is in the lead port and the lead engaging mechanism is in the closed position. The brake is in a second position where it is not frictionally coupled with the lead when the terminal connector is in the lead port and the lead engaging mechanism is in the open position.

In some embodiments, terminal connector is removably held in the lead port when the brake is frictionally coupled with the lead.

In some embodiments, the distal end of the lead is implanted in tissue at a distal site, and the terminal connector is removably held in the lead port when the brake is frictionally coupled with the lead such that the force required to remove the terminal connector from the lead port is less than the force required to dislodge the lead from the distal site.

In some embodiments, the brake comprises a material with a durometer between 30 and 100 on the Shore D scale.

In some embodiments, the brake comprises a material with a durometer between 65 and 75 on the Shore D scale.

In some embodiments, the brake comprises an elastomer.

In some embodiments, the elastomer is silicone.

In some embodiments, the lead further comprises a retention sleeve, and the brake is frictionally coupled with the retention sleeve when the terminal connector is in the lead port, the lead engaging mechanism is in the closed position, and the at least one contact is aligned with the at least one terminal contact.

In some embodiments, the at least one contact is spring loaded.

In some embodiments, the lead engaging mechanism comprises a cam configured to axially displace the at least one contact between the open position and the closed position.

In some embodiments, the lead engaging mechanism comprises a knob, a cam, and a cam follower. The cam is rotatable by the knob. The cam follower is biased against the cam. The cam follower is responsive to the cam such that rotating the cam axially-displaces the cam follower between the open position and the closed position. The at least one contact is coupled to the cam follower and moves responsive to the motion of the cam follower.

In some embodiments, the cam comprises a first ramp which is disposed circumferentially around the axis of rotation of the cam.

In some embodiments, the cam follower comprises a second ramp which is disposed circumferentially around the axis of rotation of the cam. The cam axially displaces the cam follower by sliding the slope of the first ramp against the slope of the second ramp.

In some embodiments, the interface comprises a printed circuit board. The cam follower attaches to the printed circuit board and the at least one contact is mounted on the printed circuit board.

In some embodiments, the lead engaging mechanism further comprises a first detent. The first detent is configured to bias the lead engaging mechanism into the closed position.

In some embodiments, the lead engaging mechanism further comprises a first indexing pin. The first indexing pin moves responsive to rotation of the knob. The housing has a first indexing opening. The first indexing pin extends into the first indexing opening. The first indexing opening is configured such that the first indexing pin moves along the length of the first indexing opening as it moves responsive to rotation of the knob. The first detent biases the first indexing pin into a position in the first indexing opening corresponding to the closed position for the lead engaging mechanism.

In some embodiments, the lead engaging mechanism further comprises a second indexing pin. The second indexing pin moves responsive to rotation of the knob. The housing has a second indexing opening. The second indexing opening is configured such that the second indexing pin moves along the length of the second indexing opening as it moves responsive to rotation of the knob. The second indexing opening has a detent which biases the second indexing pin into a position in the second indexing opening corresponding to the open position for the lead engaging mechanism.

In some embodiments, the first indexing opening has a second detent. The second detent biases the first indexing pin into the position corresponding to the open position for the lead engaging mechanism. The first detent biases the first indexing pin into the position corresponding to the closed position for the lead engaging mechanism.

In some embodiments, the lead further comprises a retention sleeve. The housing further comprises an alignment window. The alignment window extends from the outer surface of the housing to the lead port at a location on the lead port where the retention sleeve of the lead is visible through the alignment window when the at least one contact is aligned with the at least one terminal contact.

In some embodiments, the interface comprises a brake which moves responsive to the lead engaging mechanism. The brake contacts the retention sleeve when the terminal connector is in the lead port, the lead engaging mechanism is in the closed position, and the retention sleeve is visible through the alignment window.

In some embodiments, the lead port comprises an aperture in the housing and a channel extending into the housing from the aperture and having a lead stop inside the housing and at the end of the channel opposite the aperture. The aperture and the channel have a diameter larger than the diameter of the terminal connector. The channel has a first opening configured to allow the at least one contact to be in electrical communication with the at least one terminal contact when the lead engaging mechanism is in the closed position and the terminal connector is in the lead port.

In some embodiments, the interface comprises a brake which moves responsive to the lead engaging mechanism. The first opening is configured to allow the brake to frictionally couple with the lead when the terminal connector is in the lead port and the lead engaging mechanism is in the closed position.

In some embodiments, the interface comprises a brake which moves responsive to the lead engaging mechanism. The channel has a second opening along its length configured to allow the brake to frictionally couple with the lead when the terminal connector is in the lead port and the lead engaging mechanism is in the closed position.

In some embodiments, the lead further comprises a stylet or stiffening wire, and the housing further comprises a slot. The slot has a width less that the diameter of the terminal connector but greater than the diameter of the stylet or stiffening wire. The slot extends laterally from the channel to the outside of the housing. The slot extends longitudinally from the aperture, along the length of the channel up to the lead stop, and beyond the stop to the side of the housing opposite the aperture.

In some embodiments, a second lead has a terminal connector at its proximal end. The terminal connector of the second lead has at least one terminal contact. The interface further comprises one or more additional contacts. The housing comprises a second lead port, the second lead port being configured to receive the terminal connector of the second lead. The one or more additional contacts move responsive to the lead engaging mechanism, wherein the second contact is in a position to couple to a terminal contact of the terminal connector of the second lead when the terminal connector of the second lead is in the second lead port and the lead engaging mechanism is in the closed position Another aspect of the present disclosure relates to an interface for coupling to a lead. The lead has a terminal connector at the proximal end of the lead. The terminal connector has at least one terminal contact. The interface comprises a housing, a lead engaging mechanism, at least one contact, and a brake. The housing comprises a lead port. The lead port comprises an aperture in the housing and a channel. The channel extends into the housing from the aperture and has a lead stop inside the housing and at the end of the channel opposite the aperture. The aperture and the channel have a diameter larger than the diameter of the terminal connector. The lead engaging mechanism comprises a knob, a cam, and a cam follower. The cam is rotatable by the knob. The cam follower is biased against the cam and is responsive to the cam such that rotating the cam axially-displaces the cam follower between an open position and a closed position. The at least one contact moves responsive to the cam follower, wherein the at least one contact is in a position to be in electrical communication with the at least one terminal contact when the cam follower is in the closed position and the terminal connector is in the lead port. The brake moves responsive to the cam follower, wherein the brake is in a position where it is frictionally coupled with the lead when the cam follower is in the closed position and the terminal connector is in the lead port, and wherein the brake is in a position where it is not frictionally coupled with the lead when the cam follower is in the open position and the terminal connector is in the lead port.

Another aspect of the present disclosure relates to a system for connecting to a percutaneously implantable medical lead, the system comprising an interface as discussed above, a test device, and a cable configured to connect the interface to the test device such that the test device is in electrical communication with the at least one contact.

In some embodiments, the test device is an external pulse generator.

Another aspect of the present disclosure relates to a method of securing a terminal connector of a lead in an interface. The terminal connector comprises one or more terminal contacts. The interface comprises a housing with a lead port. The method comprises inserting the terminal connector into the lead port; rotating a knob, wherein the knob is coupled to a cam; rotating the cam, wherein the cam is coupled to a cam follower; and moving the cam follower into a closed position, wherein the cam follower is coupled to one or more contacts. Moving the cam follower into a closed position causes the one or more contacts to be positioned in electrical communication with the one or more terminal contacts.

In some embodiments, the cam follower is coupled to a brake, and moving the cam follower into a closed position causes the brake to be in frictional coupling with the lead.

In some embodiments, moving the cam follower into a closed position further comprises biasing a first indexing pin into a position corresponding to the closed position using a first detent.

In some embodiments, rotating the knob comprises overcoming the bias of a second detent on a second indexing pin.

In some embodiments, the lead port comprises an aperture in the housing, a channel, and a lead stop at the end of the channel opposite the aperture. The lead further comprises a stylet or stiffening wire protruding from the terminal connector, the stylet or stiffening wire having an exposed length, the exposed length being the portion of the stylet or stiffening wire between the proximal end of the stylet or stiffening wire and the terminal connector. The housing further comprises a slot, the slot having a width less that the diameter of the terminal connector but greater than the diameter of the stylet or stiffening wire, the slot extending laterally from the channel to the outside of the housing, the slot extending longitudinally from the aperture, along the length of the channel up to the lead stop, and beyond the lead stop to the side of the housing opposite the aperture. Inserting the terminal connector into the lead port further comprises passing the exposed length of the stylet or stiffening wire through the slot.

In some embodiments, the lead further comprises a retention sleeve. The lead port further comprises an alignment window extending from the outer surface of the housing to the channel. The method of securing a terminal connector of a lead in an interface further comprises verifying that the retention sleeve is aligned with the alignment window.

These and other features, aspects, and advantages of the present invention will become better understood with regard to the following description, appended claims, and accompanying drawings.

BRIEF DESCRIPTION OF THE DRAWINGS

So that the present disclosure can be better understood, a detailed description is provided below that makes reference to features of various embodiments, some of which are illustrated in the appended drawings. The appended drawings, however, merely illustrate the more pertinent features of the present disclosure and are not intended to limit the scope of the invention.

Figure 1A:
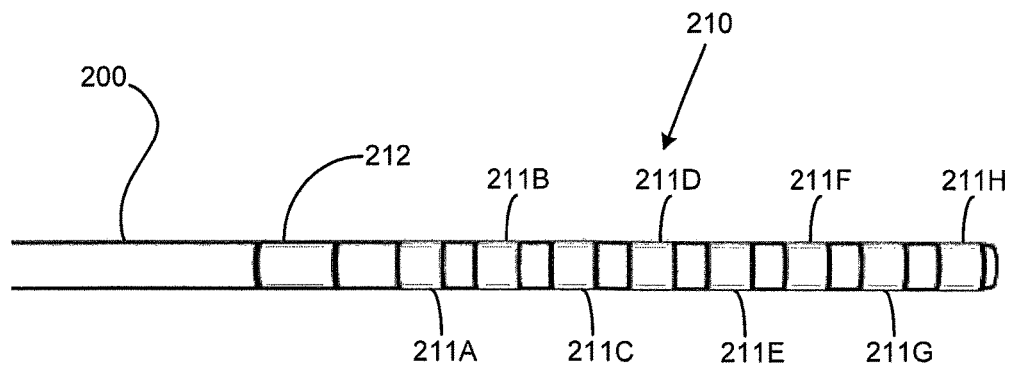
FIG. 1A is a side view of an embodiment of a terminal connector of a lead.

Some of the drawings may not depict all of the components of a given method or apparatus. In addition, like reference numerals may be used to denote like features throughout the specification and figures. In some instances where a feature is repeated multiple times, only one of the features is labeled. In the figures and the following description, some reference numerals are followed by a letter suffix. The reference numeral refers to the feature generally, whereas the reference numeral with the letter suffix is used to differentiate between different instances of the same feature within an embodiment; these letter suffixes are meant to be illustrative, and do not limit the claims.

DETAILED DESCRIPTION

FIG. 1A is a side view of an embodiment of a terminal connector 210 of a lead 200. The terminal connector 210 is located at the proximal end of the lead 200. It includes at least one, and usually plural, terminal contacts 211 for providing electrical communication with electrodes at the distal end of the lead 200. In some embodiments, the lead 200 includes a retention sleeve 212. When the lead 200 is connected to a long-term or permanent device, the retention sleeve 212 serves as a contact point for a connecting mechanism, such as a set screw, to contact the lead 200, holding it into the long-term implantable medical device connector.

Figure 1B:
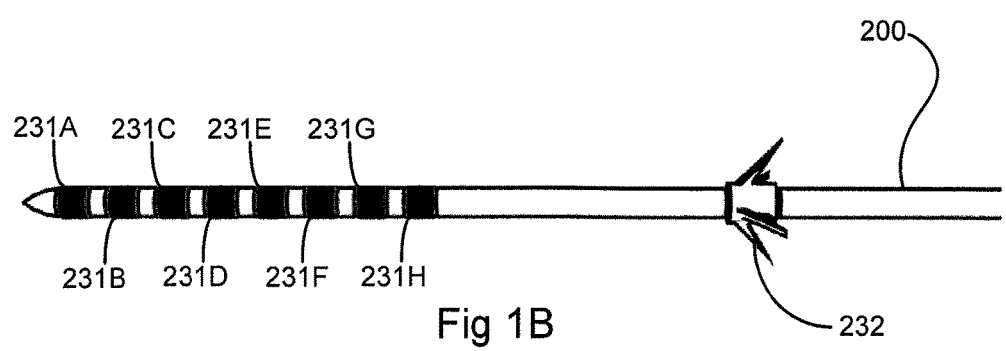
FIG. 1B is a side view of an embodiment of a distal end of a lead.

FIG. 1B is a side view of an embodiment of a distal end of a lead 200. The distal end of the lead 200 includes at least one electrode 231 corresponding to each terminal contact 211. Each electrode 231 is in electrical communication with a terminal contact 211 of the lead. In some embodiments, the distal end of the lead 200 includes an anchor 232. The anchor 232 holds the distal end of the lead 200 at an implantation site in tissue. In some embodiments, a percutaneously implanted lead is additionally or alternatively sutured, clamped, or otherwise fixed near the site of penetration of the skin.

Figure 2:
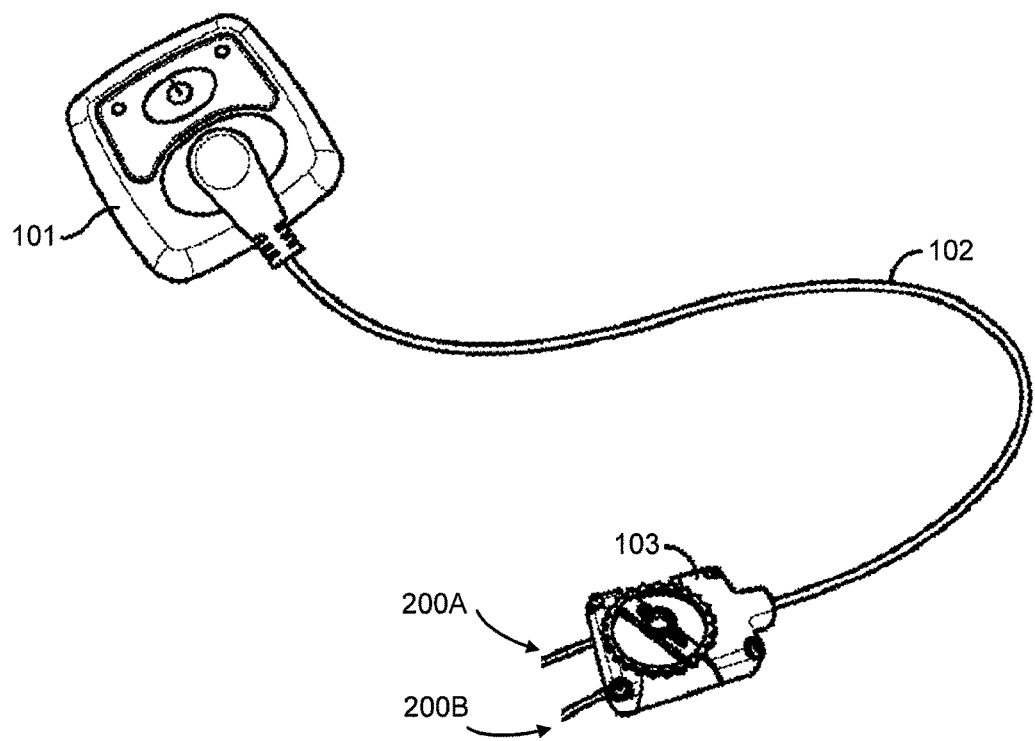
FIG. 2 shows an embodiment of a system for connecting to a percutaneously implantable lead.

FIG. 2 shows an embodiment of a system for connecting to a percutaneously implanted lead. This system includes an external device 101, a cable 102, and an interface 103. In some embodiments, the external device is an external pulse generator ('EPG'). The cable 102 connects with the external device 101 at one end and with the interface 103 at the other. The interface 103 includes a lead port which is configured to receive a terminal connector 210 of a lead. The interface 103 also includes a lead engaging mechanism which has an open position and a closed position. At least one contact 702 moves responsive to the lead engaging mechanism. When a terminal connector 210 of a lead is in the lead port when the lead engaging mechanism is in the closed position, the at least one contact 702 is in electrical communication with the at least one terminal contact 211, so accordingly the interface is in electrical communication with the terminal contacts 211 of the lead, and can thereby provide electrical communication between the external device 101 and the lead 200.

Figure 3A:
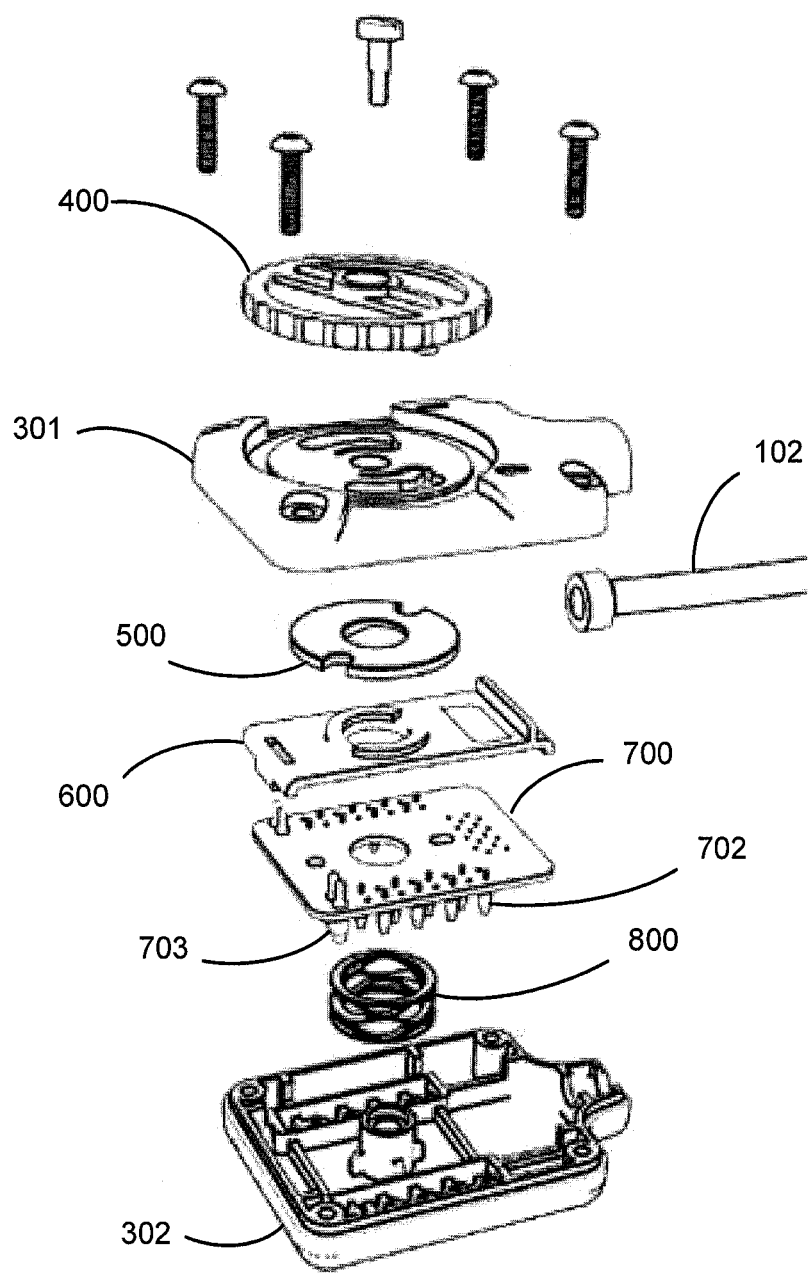
FIG. 3A is a perspective exploded view of an embodiment of an interface.

FIG. 3A is a perspective exploded view of an embodiment of an interface. In some embodiments, the interface 103 includes a knob 400, a housing 300 with a top portion 301 and a bottom portion 302, a cam 500, a cam follower 600, a printed circuit board ('PCB') 700, a spring 800, and a cable 102. In some embodiments, at least one brake 703 and at least one contact 702 may be attached to the PCB. The top portion 301 and bottom portion 302 of the housing enclose the cam 500, cam follower 600, PCB 700, spring 800, and one end of the cable 102. The knob 400 is attached to the outside of the top portion 301 of the housing.

Figure 3B:
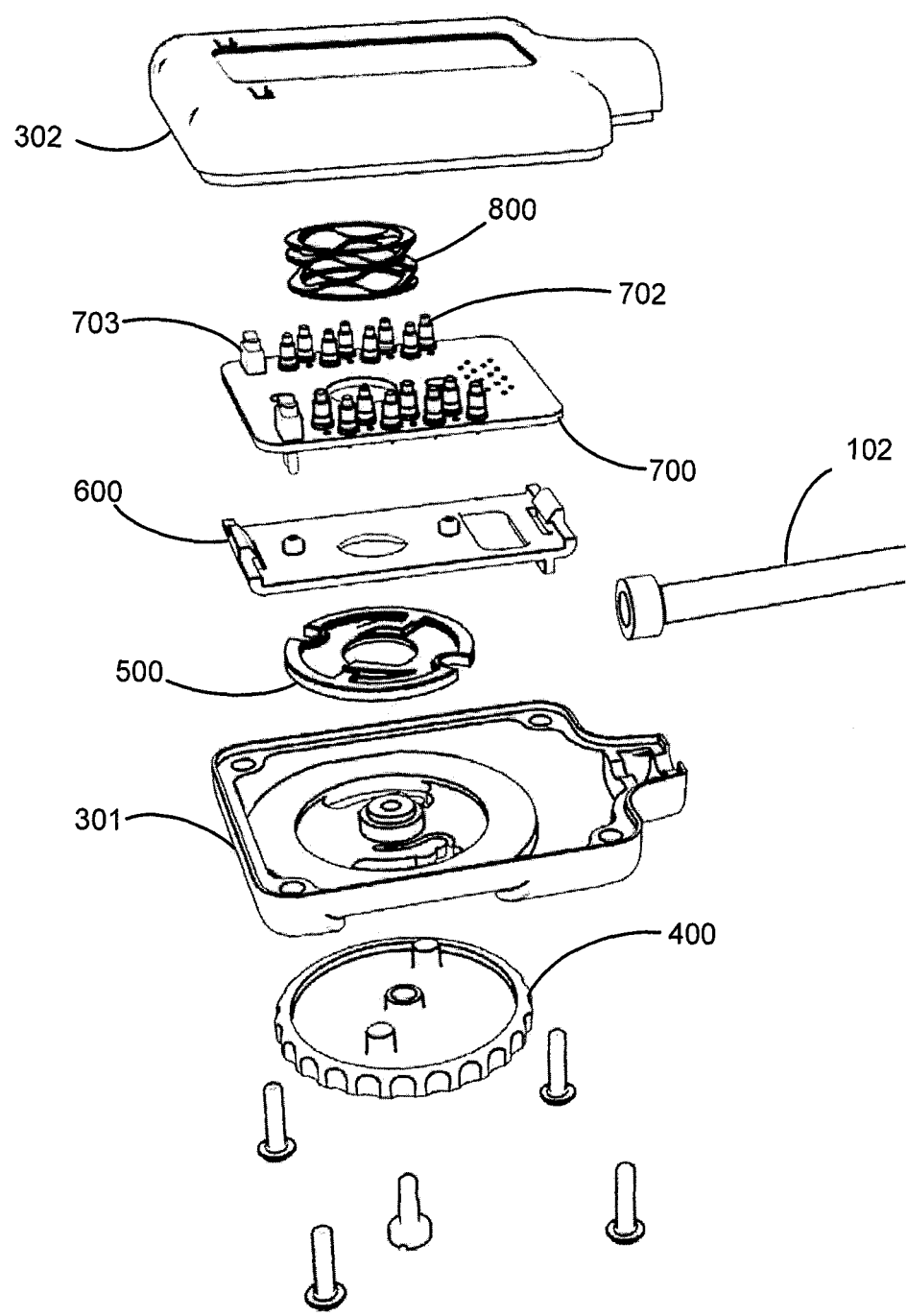
FIG. 3B is a different perspective exploded view of the embodiment of an interface from FIG. 3A.

FIG. 3B shows the exploded view of the embodiment shown in 3B from a different angle. In particular, FIG. 3B provides a view of the bottom surfaces of the knob 400, the top portion 301 and bottom portion 302 of the housing, the cam 500, the cam follower 600, and the PCB 700. The at least one brake 703 and at least one contact 702 are on the bottom surface of the PCB 700.

Figure 4A:
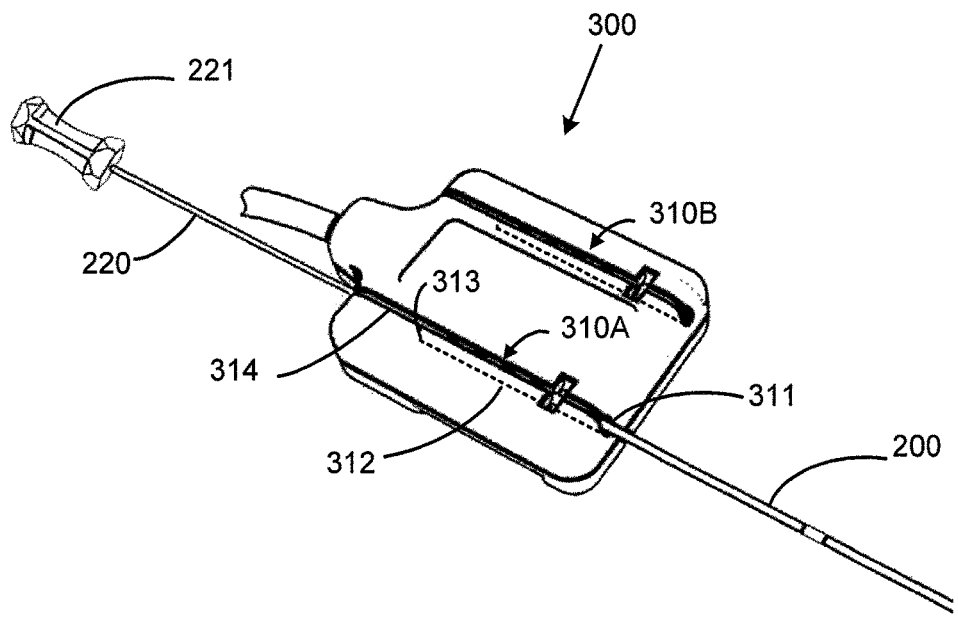
FIG. 4A is a perspective view of an embodiment of an interface.

FIG. 4A is a perspective view of an embodiment of an interface according to the invention. In some embodiments, the housing 300 defines two lead ports 310A, 310B for the lead or leads 200 to be tested. Alternative embodiments may include only one lead port 310, or may include more than two lead ports. In some embodiments, each lead port 310 comprises a channel 312 running through the housing 300. The channel 312 runs from an aperture 311 in the housing 300 up to a lead stop 313 within the housing 300. The channel 312 has a diameter slightly larger than the terminal connector 210 of the lead, and is generally configured to receive the terminal connector 210. The terminal connector 210 of a lead may be inserted through the aperture 311 and slid down the channel 312 until it reaches the lead stop 313 at the end of the channel.

In some embodiments, the one or more terminal contacts 211 are aligned with the one or more interface contacts 702 when the proximal end of the terminal connector 210 is in contact with the lead stop 313.

In some embodiments, the lead port 310 also has a stylet slot 314. The stylet slot 314 allows a lead 200 with a stylet 220 to be inserted into or removed from the interface 103 without removing the stylet 220. The stylet 220 would typically protrude from the proximal end of the lead 200 and be attached to a steering mechanism 221. The stylet 220 would have a diameter less than the diameter of the lead 200, but the steering mechanism 221 may have a diameter greater than the diameter of the lead 200. Accordingly, the steering mechanism 221 would not be able to fit down the channel 312 of the lead port. In some embodiments, the stylet slot 314 has a width which is smaller than the diameter of the lead 200, so the lead 200 cannot enter or exit the channel 312 through the stylet slot 314, but larger than the diameter of the stylet 220. In some embodiments, the stylet slot 314 provides an opening between the channel 312 and the outside of the housing 300 which starts at the aperture 311, extends the length of the channel 312, and extends beyond the end of the channel to the end of the housing 300. The portion of the slot 314 disposed beyond the end of the channel and to the end of the housing 300 allows the stylet 220 to extend straight out, coaxially with the channel 312, from the proximal end of the lead 200. In some embodiments where a lead 200 with a stylet 220 is inserted into the lead port 310, when the proximal end of a lead 200 is inserted into the aperture 311 of the channel, the stylet 220 extends from the channel 312 through the stylet slot 314 to the outside of the housing 300 and to the steering mechanism 221. This allows the steering mechanism 221 to remain outside the housing 300, while allowing the lead 200 to be inserted into or removed through the aperture 311 while the stylet 220 and steering mechanism 221 are still attached.

In some embodiments, the stylet slot 314 may additionally or alternatively allow a lead with a stiffening wire to be inserted into or removed from the interface without removing the stiffening wire. Although the stiffening wire may not include a steering mechanism, using the stylet slot 314 to insert a lead with a stiffening wire protruding from the proximal end of the terminal connector may be easier than threading the stiffening wire through the channel 312.

Figure 4B:
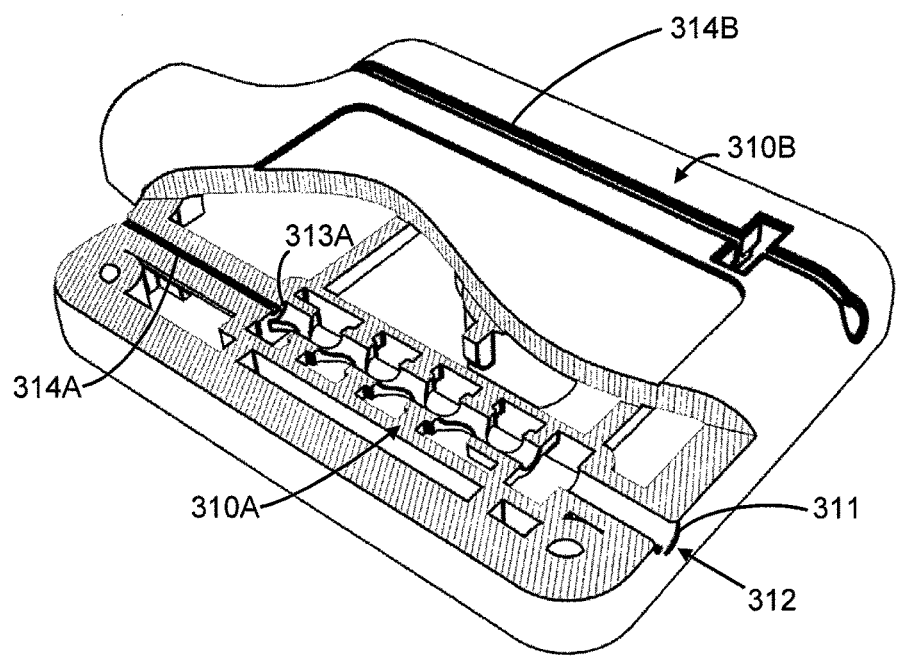
FIG. 4B is a perspective view of a cutaway of an embodiment of an interface.

FIG. 4B shows a cutaway of an embodiment of an interface, showing a cross section of a portion of a housing 300 containing a lead port 310A. The aperture 311 and the lead stop 313 can be seen at both ends of the channel 312 of the lead port 310A. A shallow portion of the stylet slot 314A can also be seen. The portion of the stylet slot 314A visible in FIG. 7B is the bottom of the portion of the stylet slot 314A which extends beyond the lead stop 313 to the end of the housing 300 opposite the aperture 311. As can be seen by comparing the lead port 310A to the lead port 310B which is not cut away, the stylet slots 314A, 314B extend laterally to the outside surface of the housing 300 and extend longitudinally from the aperture 311, along the length of the channel 312 up to the lead stop 313 and beyond the lead stop 313 to the end of the housing opposite the aperture 311.

Figure 5:
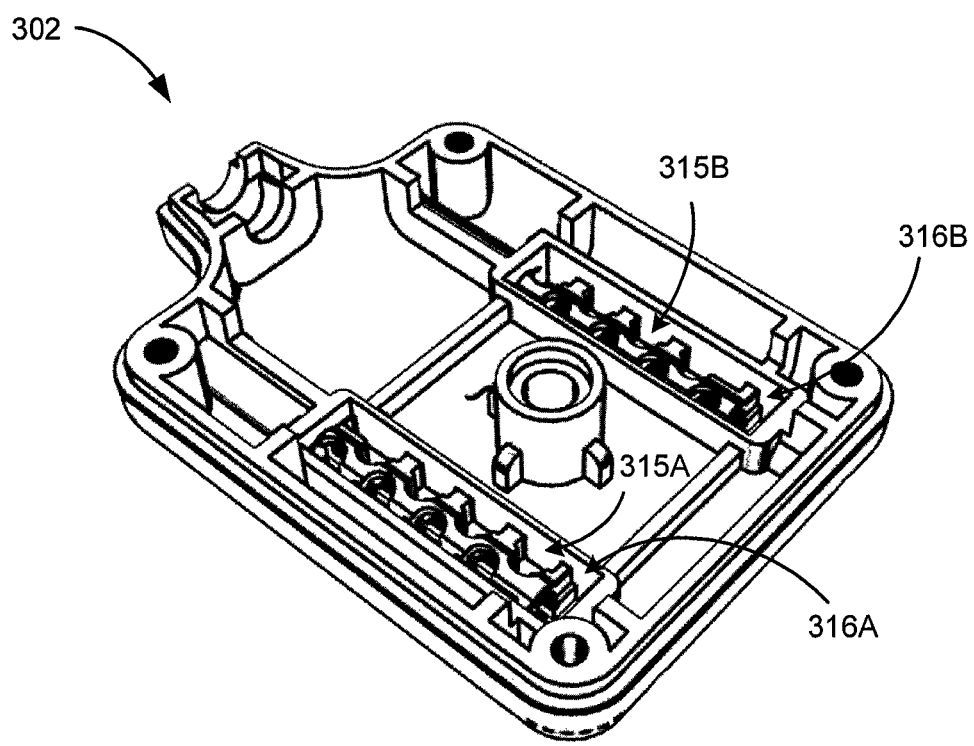
FIG. 5 is a perspective view of the inner face of the bottom portion of the housing of an interface according to some embodiments.

FIG. 5 is a perspective view of the inner face of the bottom portion 302 of a housing of an interface according to some embodiments. In some embodiments, there are openings 315 on the inside of the housing running to the channel 312 which provide access to the terminal contacts 211 of a lead when the terminal connector 210 is properly placed in the lead port 310. These openings 315 allow contacts 702 of the interface to enter the channel and make electrical contact with the terminal contacts 211. Note that while several openings 315 are present on each lead port 310 in the embodiment shown in FIG. 4, only one such opening 315A, 315B is labeled for each lead port. In some embodiments, the bottom portion 302 of the housing includes one opening 315 for each contact 702 in the connector. In alternative embodiments, one opening 315 may provide access to the channel for multiple contacts 702 or all of the contacts 702 corresponding to a given lead port 310.

In some embodiments, there is an additional opening 316 on the inside of the housing running to the channel 312 This additional opening 316 allows a brake 703 to enter the channel 312 and frictionally couple with a lead 200 in the lead port 310. In some embodiments, the additional opening 316 aligns with the retention sleeve 212 when the terminal connector 210 is properly aligned in the lead port 310 and allows a brake 703 to enter the channel 312 and frictionally couple with the retention sleeve 212. In some embodiments, the additional opening 316 provides access to the channel 312 for the brake 703 to contact the retention sleeve 212 and for one or more contacts 702 to make electrical contact with one or more terminal contacts 211. In some embodiments, a single opening 315, 316 provides access to the channel 312 for a brake 703 and all of the contacts 702 corresponding to a given lead port 310.

Figure 6:
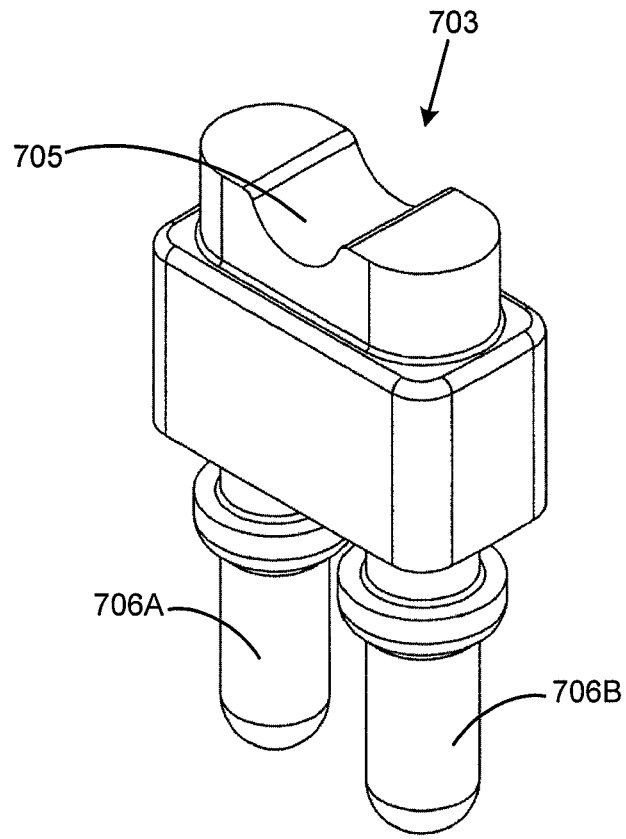
FIG. 6 is a perspective view of an embodiment of a brake.

FIG. 6 is a perspective view of an embodiment of a brake 703. In some embodiments, a brake 703 is configured to move responsive to the lead engaging mechanism. In some embodiments, when the lead engaging mechanism is in the open position, the brake 703 is not in a position to frictionally couple with a lead 200 in the lead port 310. In some embodiments, when the lead engaging mechanism is in the closed position, the brake 703 is in a position to frictionally couple with a lead 200 in the lead port 310. In some embodiments, if the terminal contacts 211 of the lead are aligned with the contacts 702 of the interface and the lead engaging mechanism is in the closed position, then the brake 703 is frictionally coupled with a retention sleeve 212 on the lead.

A brake 703 has a contacting surface 705 which makes contact with a part of the lead 200 when the brake is frictionally coupled with the lead 200. In some embodiments, the contacting surface 705 is configured to conform to the circumference of a round lead 200, thereby allowing the brake to frictionally couple with a larger area. In some embodiments, a brake 703 includes one or more brake pin 706. Brake pins 706A, 706B can be used to connect the brake 703 to a PCB 700.

In some embodiments, when a brake is frictionally coupled with a lead 200, the lead is removably held in the lead port 310. The friction prevents some levels of force from pulling the lead 200 out of the lead port 310, but allows force over a certain level to remove the lead 200 from the lead port 310 while the lead engaging mechanism is in the closed position (hereinafter 'removal force'). The value of the removal force is a design choice, and is highly configurable by a person having skill in the art. A higher removal force retains the lead more securely, but allows a higher force to be exerted on the lead (and thereby the patient) by the interface (or an object which has passed between the patient and the lead, thereby exerting force simultaneously on the lead and the interface). A lower removal force minimizes the force which can be applied to the patient and the lead by the interface but may result in the lead being released from the lead port at undesired times. The preferred level of removal force can vary based on whether the lead has an anchor 232; the type of anchor 232; how the lead 200 is clamped, sutured, or otherwise fixed near the skin penetration site; or the attachment site used for the lead 200. In some embodiments, the removal force is between 9N and 22N. In some embodiments, the removal force is between 9N and 13N. In some embodiments, the removal force is between 18N and 22N. In some embodiments, removal force is less than the force required to dislodge the lead 200 from a distal implantation site. In some embodiments, the removal force is configured based on the anchor 232 used, the fixation technique used, or the attachment site used for the lead 200.

As stated above, the removal force is configurable. It changes in response to the material of the contact surface 705, the durometer of the material of the contact surface 705, the area of contact between the contact surface 705 and the lead 200, and the pressure exerted by the brake when the lead engaging mechanism is in the closed position (in some embodiments, the pressure exerted by brake when the lead engaging mechanism is in the closed position is determined by the force of the spring 800). In some embodiments, the entire brake 703 or the portion of the brake which includes the contacting surface 705 is made of an elastomer. In some embodiments, the elastomer is silicone. In some embodiments, the entire brake 703 or the portion of the brake which includes the contacting surface 705 is made of a material with a durometer between 30 and 100 on the Shore D scale. In some embodiments, the durometer is between 65 and 75 on the Shore D scale. In some embodiments, the durometer is between 35 and 65 on the Shore D scale. In some embodiments, the durometer is between 75 and 95 on the Shore D scale.

Figure 7:
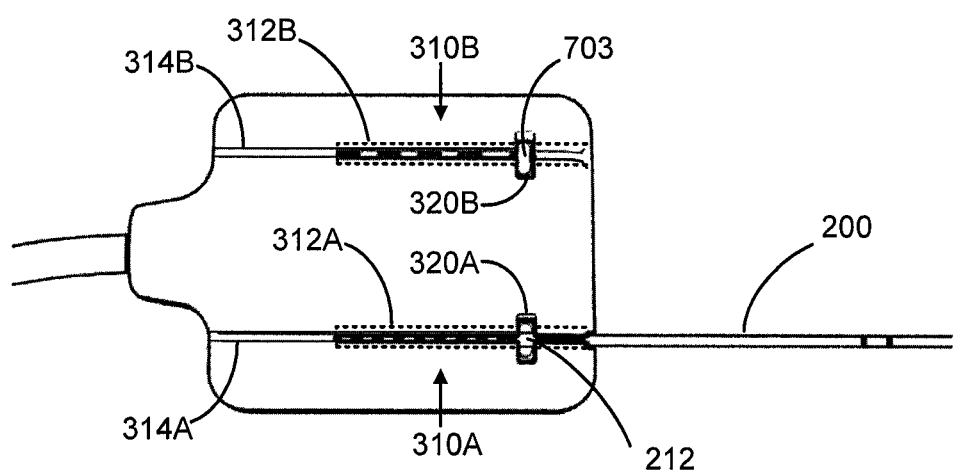
FIG. 7 is a bottom view of an embodiment of an interface.

FIG. 7 is a bottom view of an embodiment of an interface. In some embodiments, the housing 300 includes an alignment window 320 for each lead port 310. In some embodiments, the alignment window 320 extends from the outside of the housing 300 to the channel 312, allowing a user to see a portion of a lead 200 in the lead port 310. In some embodiments, when the terminal connector 210 is properly aligned in the lead port 310, i.e. when the terminal contacts 211 are aligned with the interface contacts 702, the retention sleeve 212 is visible in the alignment window 320. This provides a user with visual confirmation that the lead 200 is aligned properly in the interface 103.

Figure 8A:
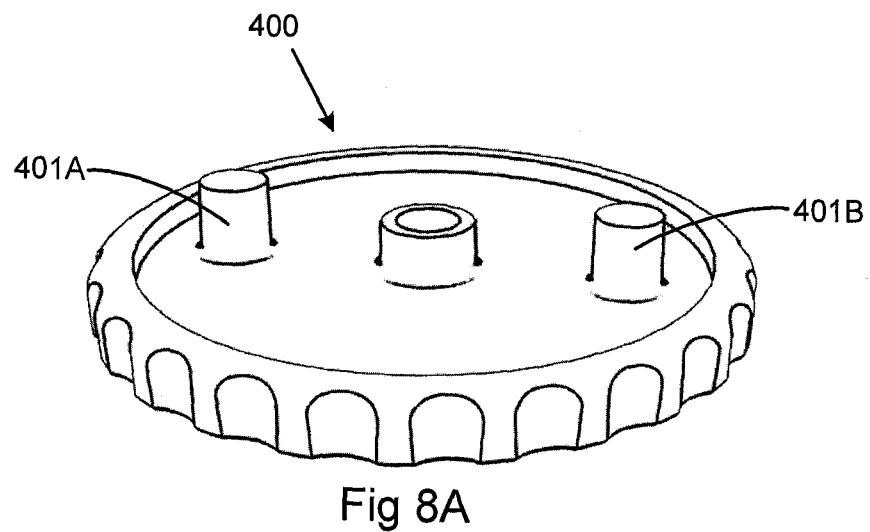
FIG. 8A is a perspective view of an embodiment of a knob.
Figure 8B:
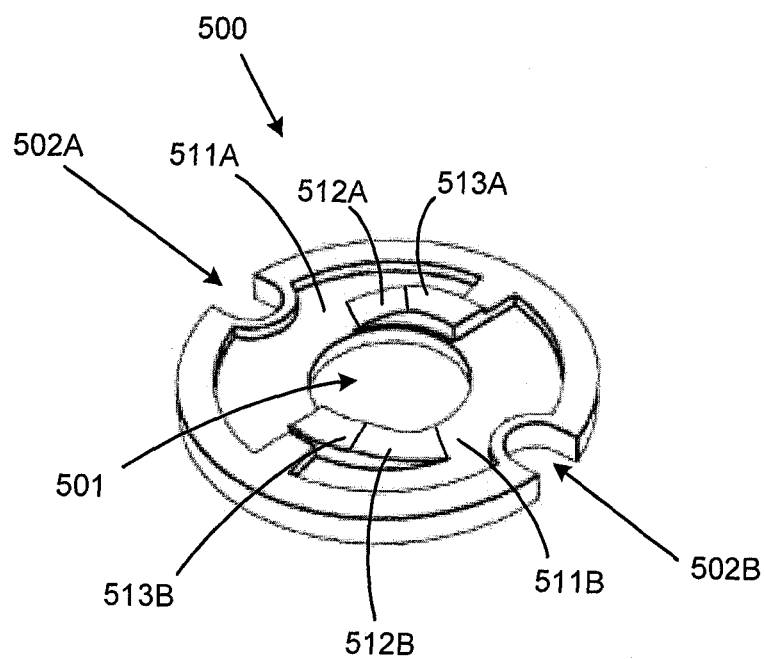
FIG. 8B is a perspective view of an embodiment of a cam.
Figure 8C:
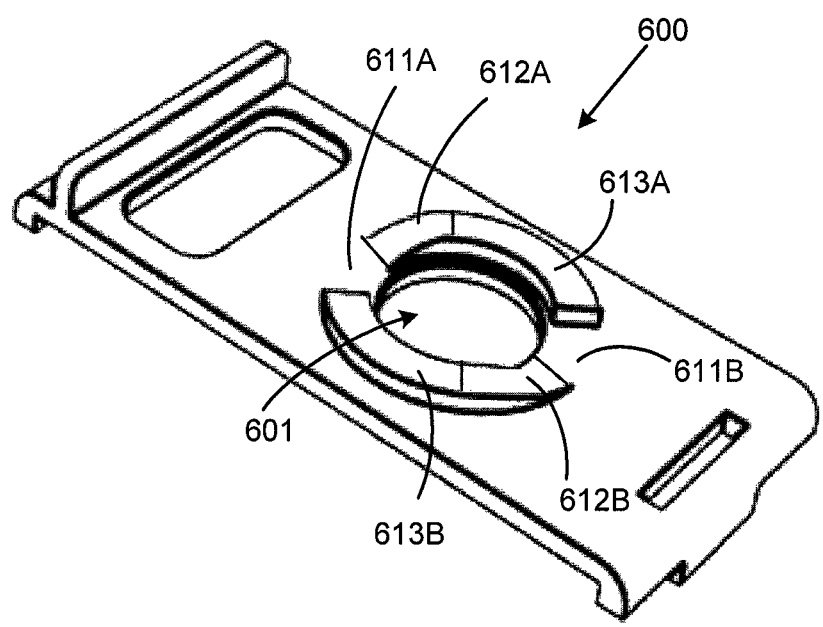
FIG. 8C is a perspective view of an embodiment of a cam follower.

FIGS. 8A-C show parts of a lead engaging mechanism according to some embodiments. Specifically, FIG. 8A shows an embodiment of a knob 400, FIG. 8B shows an embodiment of a cam 500, and FIG. 8C shows an embodiment of a cam follower 600. In some embodiments, the knob 400 has two indexing pins 401A, 401B protruding from its bottom surface.

In some embodiments, the cam 500 has a hole 501 in its center which serves as an axis of rotation. In some embodiments, the cam 500 has two notches 502A, 502B at its circumferential edge. The notches 502A, 502B are configured to line up with the indexing pins 401A, 401B protruding from the knob 400. In some embodiments, the cam 500 has two ramp elements. The ramp elements run circumferentially around the axis of rotation of the cam 500. Each ramp has a non-elevated flat surface 511, an elevated flat surface 513, and a sloped surface 512 running between the two flat surfaces 511, 513.

In some embodiments, the cam follower 600 has a hole 601 in its surface corresponding to the hole 501 in the center of the cam. In some embodiments, the cam follower 600 has two ramp elements which run circumferentially around the hole 601 in the cam follower 600. Like the ramp elements of some embodiments of the cam, these two ramp elements each have a non-elevated flat surface 611, an elevated flat surface 613, and a sloped surface 612 running between the two flat surfaces 611, 613.

Figure 9:
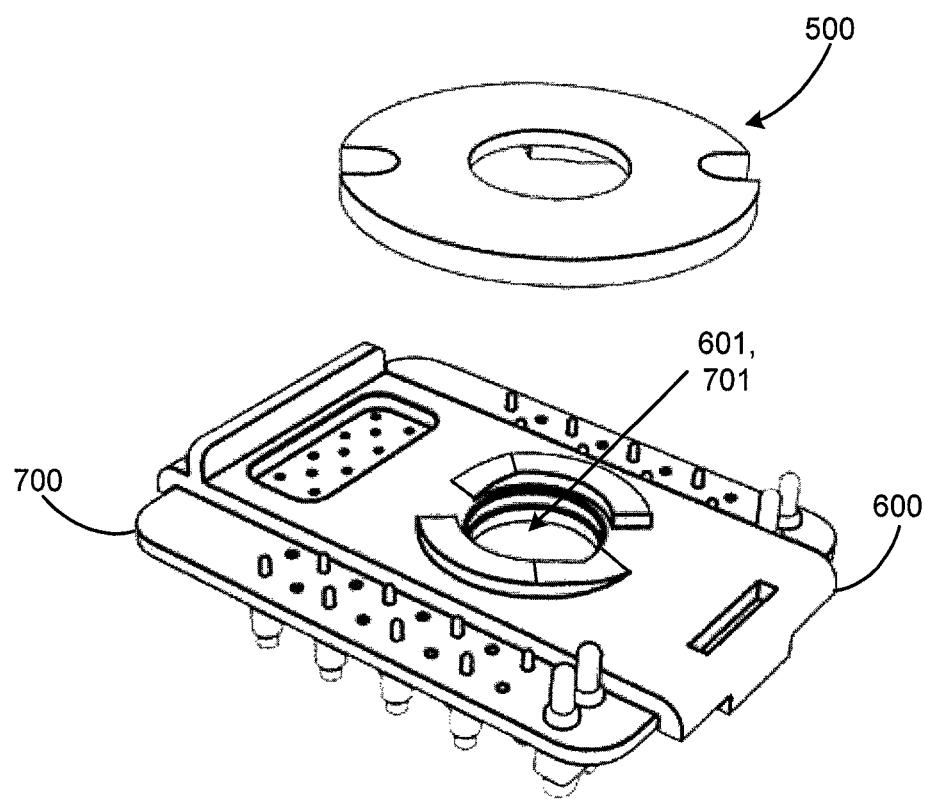
FIG. 9 is a perspective view of the cam and the cam follower of FIG. 8 wherein the surfaces with the ramp elements are disposed opposite each other.

FIG. 9 shows the cam 500 and the cam follower 600 of FIG. 8 wherein the surfaces with the ramp elements are disposed opposite each other, as they would be in an interface 103 according to some embodiments. In some embodiments, the cam follower 600 is attached to the PCB 700, and the PCB 700 has a hole 701 in its surface aligned with the hole 601 in the cam follower. In some embodiments, a shaft 340 (shown in FIG. 13) would run through the holes 501, 601, 701 in the cam, the cam follower, and the PCB. The cam 500 is free to rotate about the shaft. The cam follower 600 is rotationally fixed, so that it may move up and down the shaft 340, but may not rotate. In some embodiments, the housing 300 is shaped such that it retains the cam follower 600 or a part fixedly attached to the cam follower 600 (such as the PCB 700) to prevent the cam follower 600 from rotating. In some embodiments, the housing 300 is shaped such that the cam follower 600 or a part fixedly attached to the cam follower 600 (such as the PCB 700) can move up and down the shaft 340, but cannot rotate about the shaft 340.

The cam 500 and the cam follower 600 can be arranged in an open position or in a closed position. In some embodiments, the cam 500 and the cam follower 600 are biased against each other by a spring 800. Because the cam 500 and the cam follower 600 are biased against each other and the shaft 340 keeps the holes aligned, the ramp elements of the cam are held in contact with the ramp elements of the cam follower. In some embodiments, the cam 500 and the cam follower 600 are in the open position when the elevated flat surfaces 513, 613 are biased against the non-elevated flat surfaces 511, 611 of the opposite piece (i.e. 513 is biased against 611 and 511 is biased against 613), thereby leaving the cam 500 and the cam follower 600 in a compact configuration. In some embodiments, the cam 500 and the cam follower 600 are in the closed position when the elevated flat surfaces 513 of the cam are biased against the elevated flat surfaces 613 of the cam follower, thereby leaving the cam 500 and the cam follower 600 in a non-compact configuration. As the cam 500 rotates, the sloped surfaces 512 of the cam will slide against the sloped surfaces 612 of the cam follower, moving the cam 500 and the cam follower 600 between the open state and the closed state.

Figure 10:
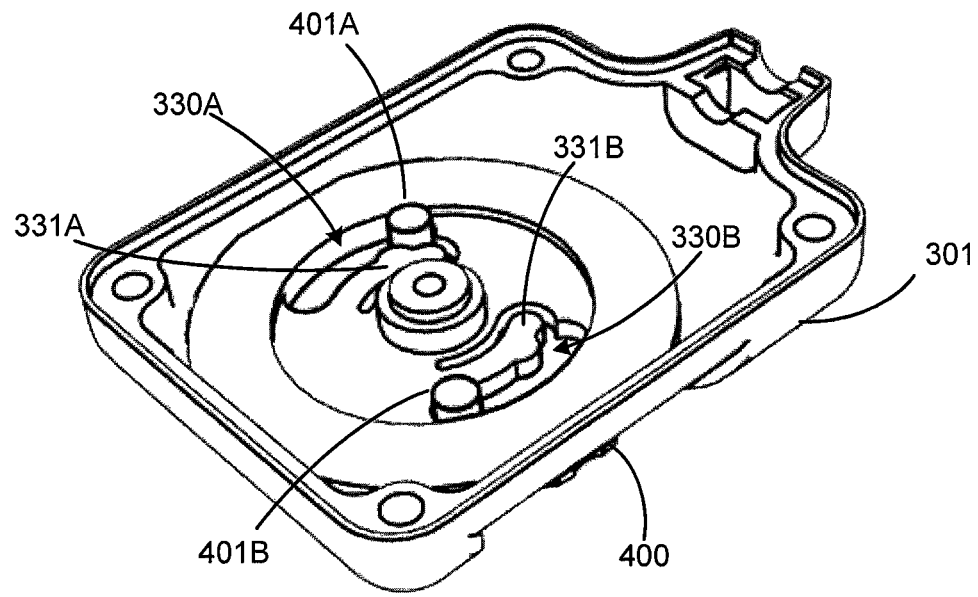
FIG. 10 shows an embodiment of the knob and the top portion of the housing.

FIG. 10 shows an embodiment of a knob 400 and a top portion 301 of a housing. In some embodiments, the housing has two indexing openings 330A, 330B. Indexing pins 401A, 401B of the knob 400 protrude through the indexing openings 330A, 330B, one pin per opening. As the knob 400 rotates, the indexing pins 401 will move longitudinally along the indexing openings 330.

Although the embodiment of FIG. 10 uses two indexing pints 401A, 401B and two indexing openings 330A, 330B, alternative embodiments use one indexing pin 401 and one indexing opening 330, and additional alternative embodiments use more than two indexing pins 401 and indexing openings 330.

Although the embodiment of FIG. 10 shows the indexing openings 330A, 330B as openings in the top portion 301 of the housing and the indexing pins 401A, 401B as protruding from the knob 400, alternative embodiments are contemplated. In some embodiments, an indexing opening 330 may be an opening in any element of an interface 103 which does not move responsive to the lead engaging mechanism and a corresponding indexing pin 401 may protrude from any element which moves responsive to the lead engaging mechanism. In alternative embodiments, an indexing opening 330 may be an opening in any element of an interface 103 which moves responsive to the lead engaging mechanism and a corresponding indexing pin 401 may protrude from any element which does not move responsive to the read engaging mechanism.

In some embodiments, the lead engaging mechanism includes a detent 331 which is configured to bias the lead engaging mechanism into the closed position. In some embodiments, each indexing opening 330 has one or more detents 331. In some embodiments, the detents 331 are deformable cantilever structures molded into the housing, running along an edge of the indexing opening 330 with a bump protruding into the indexing opening 330. As an indexing pin 401 moves along the indexing opening and contacts the bump, it will deform the cantilever until the indexing pin 401 has moved past the bump. In some embodiments, the bump is positioned near an end of the indexing opening 330, such that an indexing pin 401 can be biased into a position between the bump and the end of the indexing opening 330. In some embodiments, a detent 331 biases an indexing pin into a point in an indexing opening 330 where the position of the knob corresponds to the closed position for the cam 500 and the cam follower 600. In some embodiments, such as the embodiment shown in FIG. 10, the detent 331A of one indexing opening 330A biases an indexing pin 401A into a position where the position of the knob 400 corresponds to the closed position for the cam 500 and cam follower 600, and the detent 331B of another indexing opening 330B biases another indexing pin 401B into a position where the position of the knob 400 corresponds to the open position for the cam 500 and cam follower 600. In some embodiments, one indexing opening 330 includes multiple detents. A first detent 331 biases an indexing pin 401 into a position where the position of the knob 400 corresponds to the closed position for the cam 500 and the cam follower 600, and a second detent 331 biases the indexing pin 401 into a position where the position of the knob 400 corresponds to the open position for the cam 500 and the cam follower 600.

Figure 11:
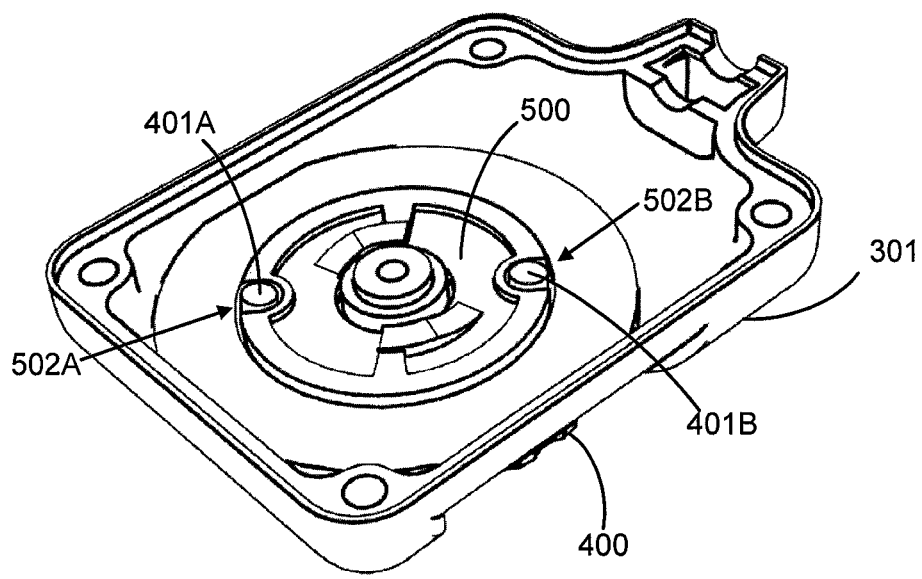
FIG. 11 shows an embodiment of the cam combined with the assembly of FIG. 10.

FIG. 11 shows an embodiment of a cam 500 combined with the knob 400 and the top portion 301 of the housing of FIG. 10. The indexing pins 401A, 401B protrude into the notches 502A, 502B in the cam, thereby causing the cam 500 to rotate when the knob 400 rotates. In alternative embodiments, movement of the cam 500 and the knob 400 are coupled by means other than an indexing pin.

Figure 12:
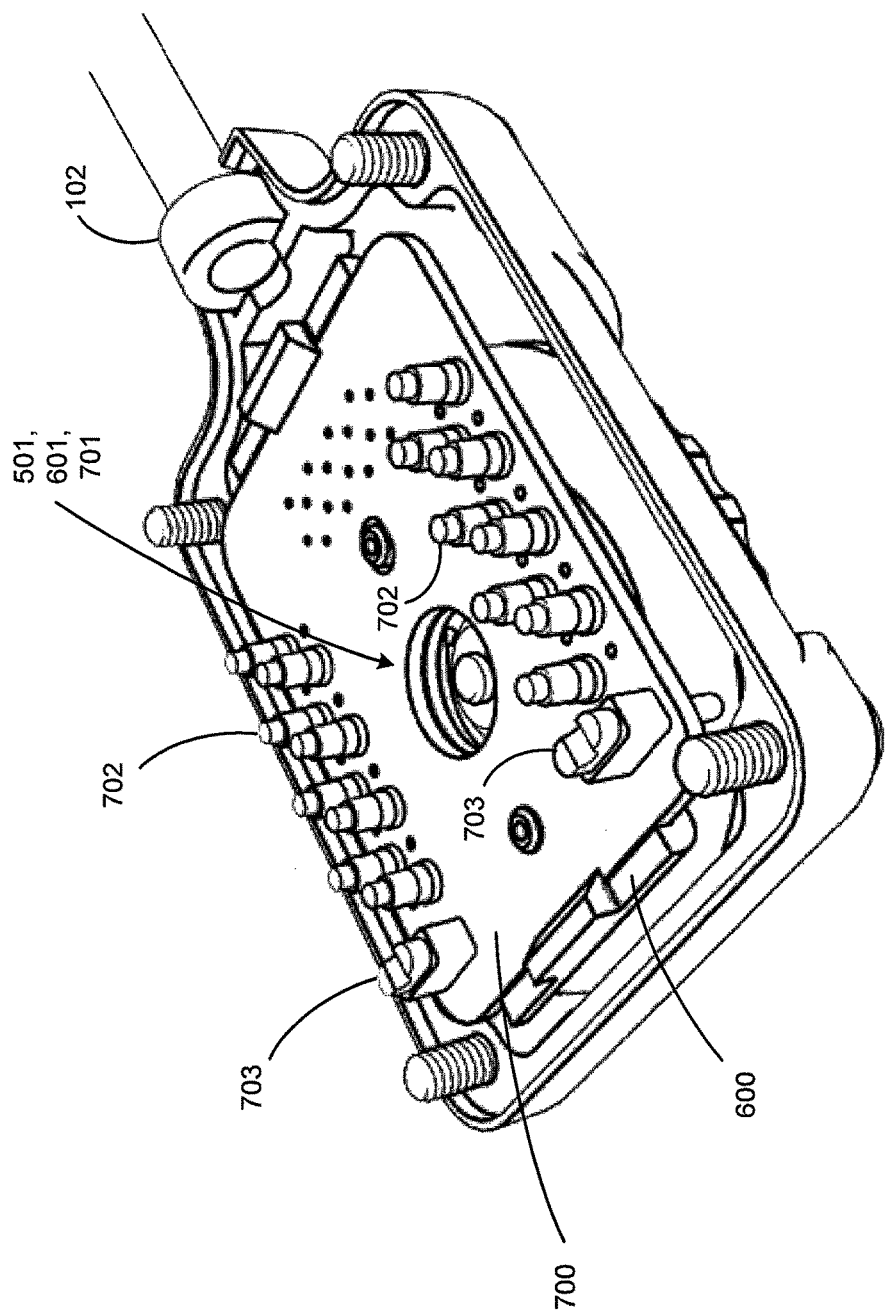
FIG. 12 shows an embodiment of the cam follower and the printed circuit board combined with the assembly of FIG. 11.

FIG. 12 shows an embodiment of the cam follower 600 and the PCB 700 combined with the assembly of FIG. 11. The ramp elements of the cam 500 and the cam follower 600 are in contact, and the holes 501, 601, 701 in the cam, the cam follower, and the PCB are aligned. In some embodiments, the brakes 703 and the contacts 702 are on the side of the PCB 700 facing away from the cam 500 and the cam follower 600, such that they will be aligned with openings 315, 316 in a lead port 310 when a bottom portion 302 of the housing containing the lead port 310 is attached to the top portion 301 of the housing. In embodiments, the contacts are spring loaded contacts. In some embodiments, the PCB 700 is wired to the cable 102 (wires not shown), providing electrical communication between the contacts 702 and an EPG 101 or other external device.

Figure 13:
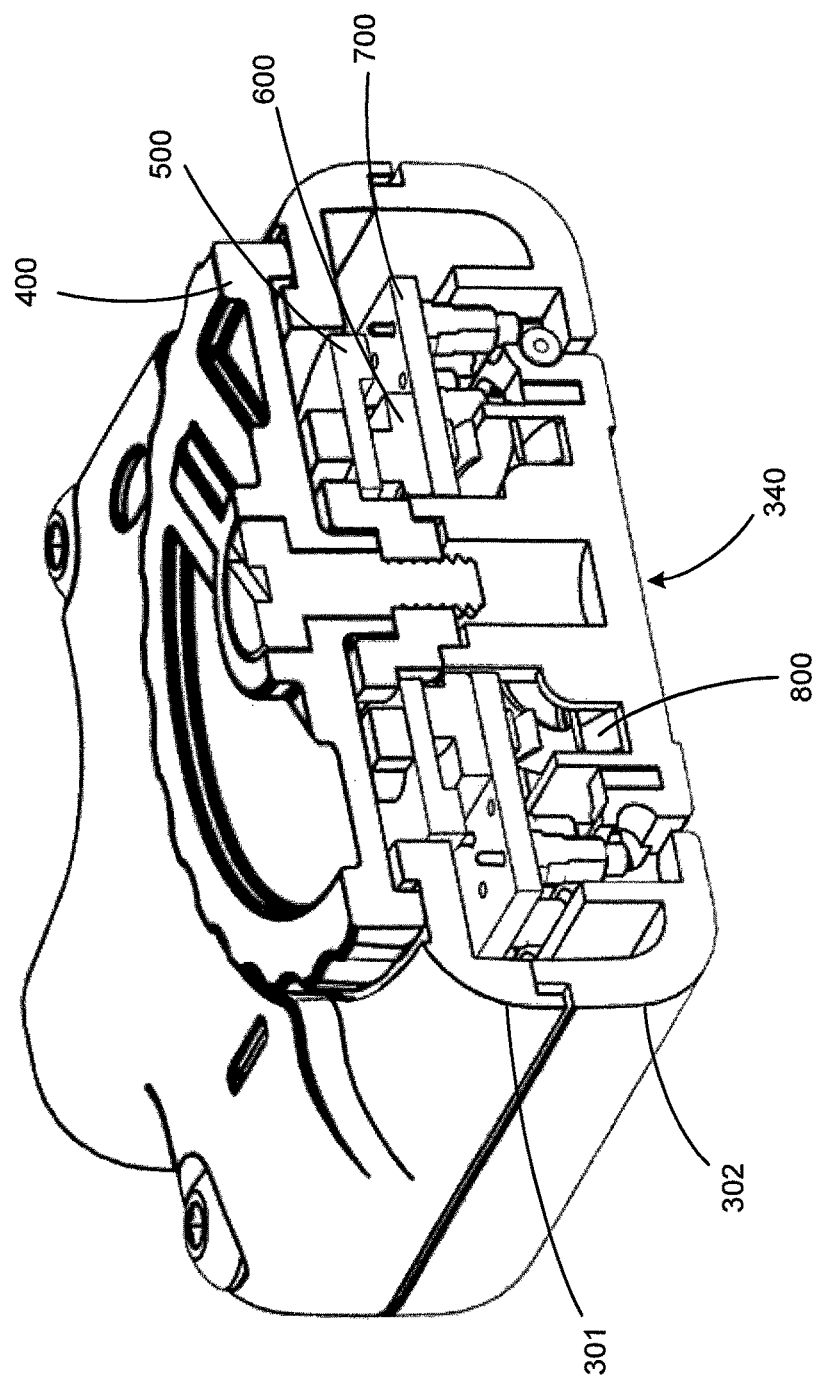
FIG. 13 shows an isometric cross sectional view of an embodiment of an interface.

FIG. 13 shows an isometric cross sectional view of an embodiment of an interface. In some embodiments, a top portion 301 and a bottom portion 302 of a housing form a shaft 340 which runs through holes 501, 601, 701 in a cam, a cam follower, and a PCB. In some embodiments, a spring 800 is compressed between the PCB 700 and the bottom portion 302 of the housing, thereby biasing the PCB 700 and the cam follower 600 against the cam 500. In some embodiments, a knob 400 is mounted on the outside of the top portion 301 of the housing.

Figure 14A:
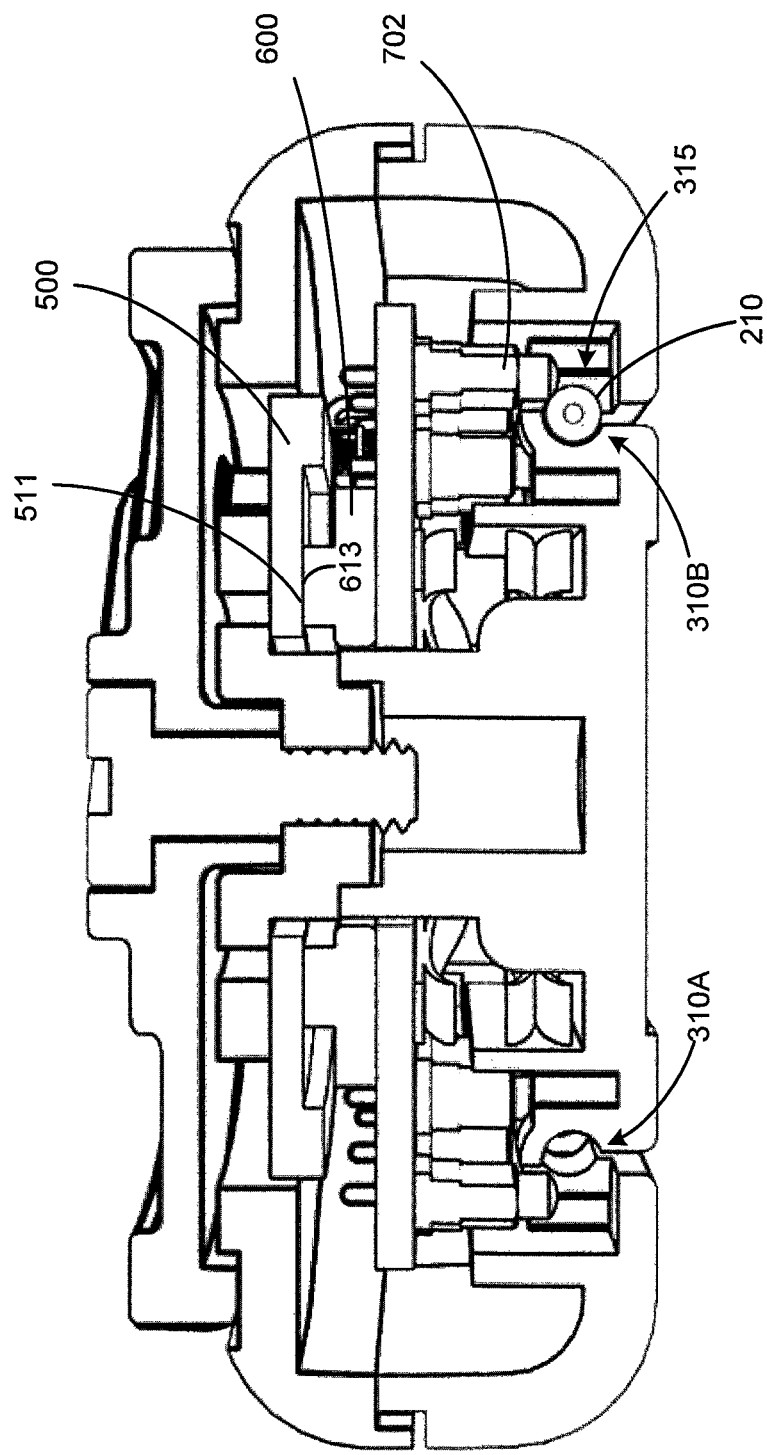
FIG. 14A shows a cross sectional view of the interface of FIG. 13 in the open position.

FIG. 14A shows a cross sectional view of an embodiment of the interface of FIG. 13 in the open position. A terminal connector 210 of a lead is in one of the lead ports 310. The elevated flat surfaces 613 of the cam follower ramp elements are contacting the non-elevated flat surfaces 511 of the cam ramp elements. This leaves the cam 500 and the cam follower 600 in as compact an arrangement as possible. Accordingly, the contacts 702 do not protrude through the openings 315 in the channel into contact with the terminal contacts 211 of the terminal connector 210.

Figure 14B:
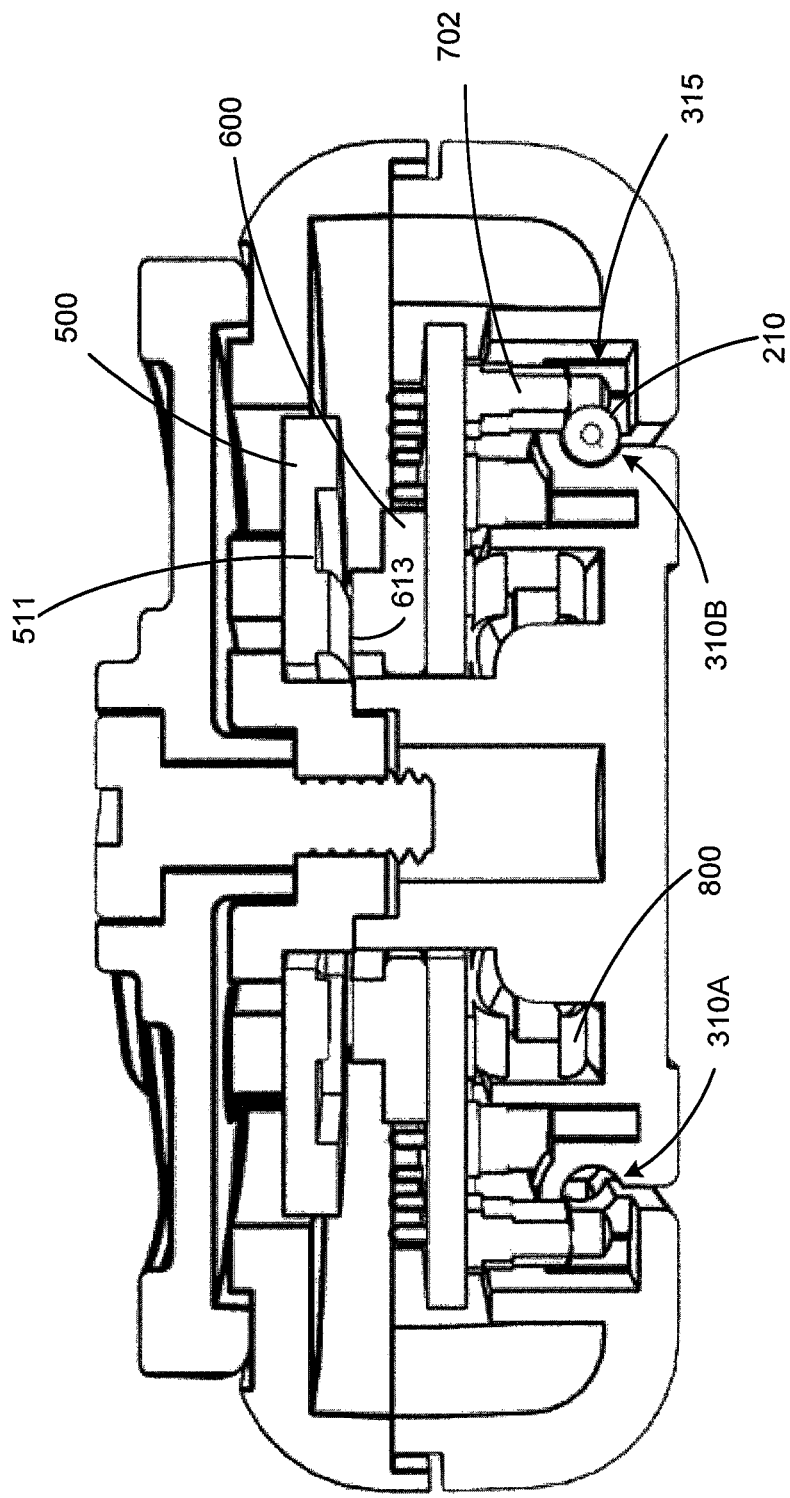
FIG. 14B shows a cross sectional view of the interface of FIG. 13 in the closed position.

FIG. 14B shows a cross sectional view of an embodiment of the interface of FIG. 13 in the closed position. The elevated flat surfaces 613 of the cam follower ramp elements are no longer in contact with the non-elevated flat surfaces 511 of the cam ramp elements. Instead, the elevated flat surfaces 613 of the cam follower ramp elements are in contact with the elevated flat surfaces 513 of the cam ramp elements (the contacting portions of these surfaces are not visible on the cross section of FIG. 14B). This pushes the cam follower 600 away from the cam 500, compressing the spring 800 and moving the contacts 702 into the openings 315 in the channel, thereby placing them in electrical communication with the terminal contacts 212 of a terminal connector 210 in the lead port 310.

Figure 15A:
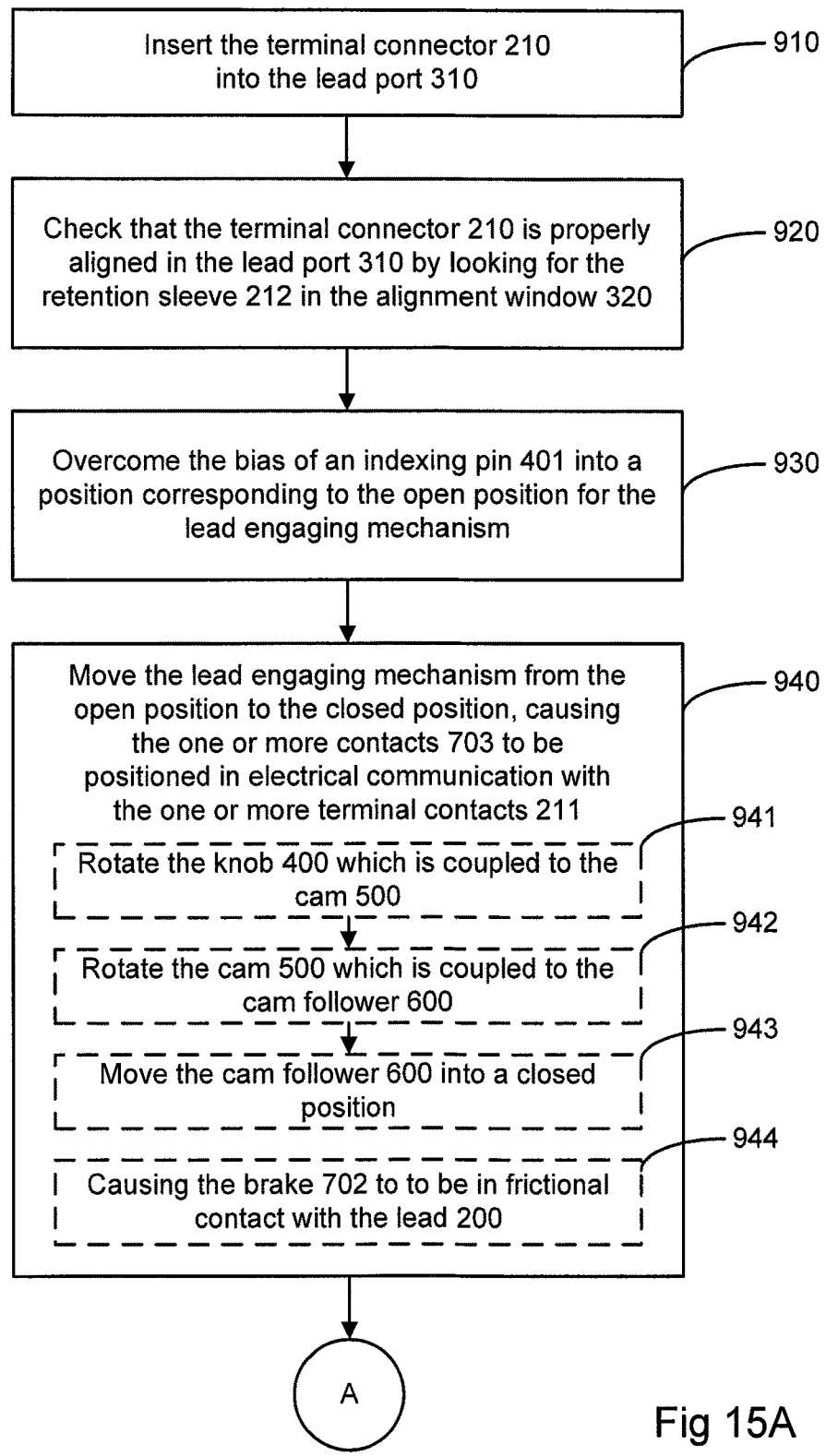
FIGS. 15A-B are flowcharts of a method of engaging a lead in an interface according to some embodiments.
Figure 15B:
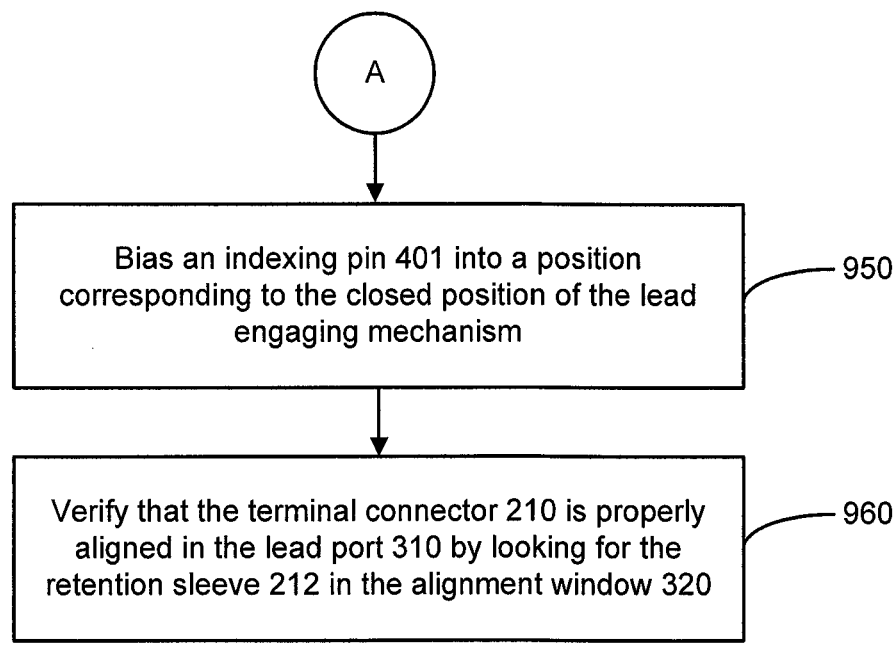

FIGS. 15A-B are flowcharts of a method of engaging a lead in an interface according to some embodiments. Throughout the description of embodiments of methods of engaging a lead in an interface, reference numerals are used which appear in previous figures. The reference numerals are illustrative, and are not intended to limit the method to use of a particular interface. Initially, a terminal connector 210 of a lead is inserted (910) into a lead port 310 in the interface 103. In some embodiments, the proximal end of the terminal connector 210 is inserted into an aperture 311 of a lead port 310, and the terminal connector 210 is slid down the lead port until one or more terminal contacts 211 on the terminal connector are aligned with corresponding one or more interface contacts 702. In some embodiments, the lead 200 has a stylet or stiffening wire 220 protruding from its proximal end. In some embodiments where the lead includes a stylet or stiffening wire 220, inserting (910) the terminal connector 210 into the lead port 310 comprises passing the portion of the stylet or stiffening wire 220 between the terminal connector 210 and proximal end of the stylet or stiffening wire 220 through a stylet slot 214.

In some embodiments, the alignment of the terminal connector 210 in the lead port 310 is checked (920) after the terminal connector 210 is inserted (910) to verify proper alignment. The terminal connector 210 is properly aligned in the lead port 310 if one or more terminal contacts 211 on the terminal connector are aligned with corresponding one or more interface contacts 702. In some embodiments, the alignment is checked (920) by looking for a retention sleeve 212 in an alignment window 320 into the lead port 310. The alignment window 320 would be configured to provide vision of the location on the channel 312 of the lead port where the retention sleeve 212 is located when the one or more terminal contacts 211 are aligned with the one or more interface contacts 702. In some embodiments, if the terminal connector 210 is not aligned properly in the lead port 310, the inserting step (910) is continued or repeated.

In some embodiments, a detent biases the lead engaging mechanism into the open position. In some embodiments, the detent 331 biases an indexing pin 401 which moves responsive to the lead engaging mechanism into a position corresponding to the open position for the lead engaging mechanism. In some embodiments, the bias of the detent 313 is overcome (930). In some embodiments, overcoming (930) the bias of the detent 313 comprises removing the indexing pin 401 from the position corresponding to the open position for the lead engaging mechanism.

Next, the lead engaging mechanism is moved (940) from an open position to a closed position. Moving (940) the lead engaging mechanism to a closed position comprises causing the one or more interface contacts 702 to be positioned in electrical communication with the one or more terminal contacts 211. In some embodiments, moving (940) the lead engaging mechanism to a closed position comprises causing (944) a brake 703 to be in frictional coupling with the lead 200.

In some embodiments, moving (940) the lead engaging mechanism from an open position to a closed position comprises rotating (941) a knob 400, rotating (942) a cam 500, and moving (943) a cam follower 600 into a closed position. The knob 400 is coupled to the cam 500 such that rotating (941) the knob 400 rotates the cam 500. The cam follower 600 is biased against the cam 500 such that rotating (942) the cam 500 moves the cam follower 600. In some embodiments, moving (943) the cam follower 600 comprises axially displacing the cam follower 600. In some embodiments, the one or more interface contacts 702 are coupled to the cam follower 600 and move responsive to the cam follower 600 such that moving (943) the cam follower 600 into the closed position causes the one or more interface contacts 702 to be in electrical communication with the one or more terminal contacts 211. In some embodiments, a brake 703 is coupled to the cam follower 600 and moves responsive to the cam follower 600 such that moving (943) the cam follower 600 into the closed position causes the brake 703 to be in frictional coupling with the lead 200.

In some embodiments, the lead engaging mechanism is biased (950) into the closed position. In some embodiments, biasing (950) the lead engaging mechanism into the closed position comprises biasing an indexing pin 401 into a position corresponding to the closed position of the lead engaging mechanism. In some embodiments, the indexing pin 401 is the same indexing pin that was biased into a position corresponding to the open position for the lead engaging mechanism, above. In alternative embodiments, it is a different indexing pin 401.

In some embodiments, the alignment of the terminal connector 210 in the lead port 310 is checked (960) after the lead engaging mechanism is moved (940) into the closed position. The terminal connector 210 is properly aligned in the lead port 310 if the one or more terminal contacts 211 are aligned with the one or more interface contacts 702. In some embodiments, the alignment is checked (960) by looking for a retention sleeve 212 in an alignment window 320 in the lead port. The alignment window 320 would be configured to provide vision of the location on the channel 312 of the lead port where the retention sleeve 212 is located when the one or more terminal contacts 211 are aligned with the one or more interface contacts 702. In some embodiments, if the terminal connector 210 is not aligned properly in the lead port 310, the lead engaging mechanism is moved from the closed position to the open position and the inserting step (910) is resumed or repeated.

The foregoing description, for purpose of explanation, has been described with reference to specific implementations. However, the illustrative discussions above are not intended to be exhaustive or to limit the claims to the precise forms disclosed. Many modifications and variations are possible in view of the above teachings. The implementations were chosen and described in order to best explain principles of operation and practical applications, to thereby enable others skilled in the art.

We claim:

1. An interface for coupling to a lead, the lead having a terminal connector at the proximal end of the lead and a retention sleeve, the terminal connector having at least one terminal contact, the interface comprising:
   a housing, the housing comprising a lead port, wherein the lead port is configured to receive the terminal connector, the housing further comprising, an alignment window, wherein the alignment window extends from the outer surface of the housing to the lead port at a location on the lead port where the retention sleeve of the lead is aligned with the alignment window when the at least one contact is aligned with the at least one terminal contact;
   a lead engaging mechanism, the lead engaging mechanism being variable between an open position and a closed position; and
   at least one contact which moves responsive to the lead engaging mechanism, wherein the at least one contact is in a position to be in electrical communication with the at least one terminal contact when the lead engaging mechanism is in the closed position and the terminal connector is in the lead port.

2. The interface of claim 1 further comprising:
   a brake which moves responsive to the lead engaging mechanism, wherein the brake is in a first position where it is frictionally coupled with the lead when the terminal connector is in the lead port and the lead engaging mechanism is in the closed position, and wherein the brake is in a second position where it is not frictionally coupled with the lead when the terminal connector is in the lead port and the lead engaging mechanism is in the open position.

3. The interface of claim 2 wherein the terminal connector is removably held in the lead port when the brake is frictionally coupled with the lead.

4. The interface of claim 2 wherein the distal end of the lead is implanted in tissue at a distal site, and the terminal connector is removably held in the lead port when the brake is frictionally coupled with the lead such that the force required to remove the terminal connector from the lead port is less than the force required to dislodge the lead from the distal site.

5. The interface of claim 2 wherein the brake comprises a material with a durometer between 30 and 100 on the Shore D scale.

6. The interface of claim 5 wherein the brake comprises a material with a durometer between 65 and 75 on the Shore D scale.

7. The interface of claim 2 wherein the brake comprises an elastomer.

8. The interface of claim 7 wherein the elastomer is silicone.

9. The interface of claim 2 wherein:
   the lead further comprises a retention sleeve; and
   the brake is frictionally coupled with the retention sleeve when the terminal connector is in the lead port, the lead engaging mechanism is in the closed position, and the at least one contact is aligned with the at least one terminal contact.

10. The interface of claim 1 wherein the at least one contact is spring loaded.

11. The interface of claim 1 wherein the lead engaging mechanism comprises a cam configured to axially displace the at least one contact between the open position and the closed position.

12. The interface of claim 1 wherein:
    the lead engaging mechanism comprises:
      a knob;
      a cam, the cam being rotatable by the knob; and
      a cam follower, the cam follower being biased against the cam, the cam follower being responsive to the cam such that rotating the cam axially-displaces the cam follower between the open position and the closed position; and
    the at least one contact is coupled to the cam follower and moves responsive to the motion of the cam follower.

13. The interface of claim 12 wherein the cam comprises a first ramp which is disposed circumferentially around the axis of rotation of the cam.

14. The interface of claim 13 wherein the cam follower comprises a second ramp which is disposed circumferentially around the axis of rotation of the cam, and wherein the cam axially displaces the cam follower by sliding the slope of the first ramp against the slope of the second ramp.

15. The interface of claim 12 further comprising a printed circuit board, wherein the cam follower attaches to the printed circuit board and the at least one contact is mounted on the printed circuit board.

16. The interface of claim 12 wherein the lead engaging mechanism further comprises a first detent, wherein the first detent is configured to bias the lead engaging mechanism into the closed position.

17. The interface of claim 16 wherein the lead engaging mechanism further comprises a first indexing pin, and wherein:
    the first indexing pin moves responsive to rotation of the knob;
    the housing has a first indexing opening;
    the first indexing pin extends into the first indexing opening;
    the first indexing opening is configured such that the first indexing pin moves along the length of the first indexing opening as it moves responsive to rotation of the knob; and
    the first detent biases the first indexing pin into a position in the first indexing opening corresponding to the closed position for the lead engaging mechanism.

18. The interface of claim 17 wherein the lead engaging mechanism further comprises a second indexing pin, and wherein:
    the second indexing pin moves responsive to rotation of the knob;
    the housing has a second indexing opening;
    the second indexing opening is configured such that the second indexing pin moves along the length of the second indexing opening as it moves responsive to rotation of the knob; and
    the second indexing opening has a detent which biases the second indexing pin into a position in the second indexing opening corresponding to the open position for the lead engaging mechanism.

19. The interface of claim 17 wherein the first indexing opening has a second detent, the second detent biases the first indexing pin into the position corresponding to the open position for the lead engaging mechanism, and the first detent biases the first indexing pin into the position corresponding to the closed position for the lead engaging mechanism.

20. The interface of claim 1 further comprising a brake which moves responsive to the lead engaging mechanism, wherein the brake contacts the retention sleeve when the terminal connector is in the lead port, the lead engaging mechanism is in the closed position, and the retention sleeve is visible through the alignment window.

21. The interface of claim 1 wherein the lead port comprises:
   an aperture in the housing; and
   a channel extending into the housing from the aperture and having a lead stop inside the housing and at the end of the channel opposite the aperture,
   wherein the aperture and the channel have a diameter larger than the diameter of the terminal connector, the channel having a first opening configured to allow the at least one contact to be in electrical communication with the at least one terminal contact when the lead engaging mechanism is in the closed position and the terminal connector is in the lead port.

22. The interface of claim 21 further comprising a brake which moves responsive to the lead engaging mechanism, wherein the first opening is configured to allow the brake to frictionally couple with the lead when the terminal connector is in the lead port and the lead engaging mechanism is in the closed position.

23. The interface of claim 21 further comprising a brake which moves responsive to the lead engaging mechanism, wherein the channel has a second opening along its length configured to allow the brake to frictionally couple with the lead when the terminal connector is in the lead port and the lead engaging mechanism is in the closed position.

24. The interface of claim 21 wherein the lead further comprises a stylet or stiffening wire, and wherein the housing further comprises:
   a slot, the slot having a width less that the diameter of the terminal connector but greater than the diameter of the stylet or stiffening wire, the slot extending laterally from the channel to the outside of the housing, the slot extending longitudinally from the aperture, along the length of the channel up to the lead stop, and beyond the stop to the side of the housing opposite the aperture.

25. The interface of claim 1 wherein a second lead has a terminal connector at its proximal end, said terminal connector of the second lead has at least one terminal contact, and the interface further comprises one or more additional contacts, wherein:
   the housing comprises a second lead port, the second lead port being configured to receive the terminal connector of the second lead; and
   the one or more additional contacts move responsive to the lead engaging mechanism, wherein the second contact is in a position to couple to a terminal contact of the terminal connector of the second lead when the terminal connector of the second lead is in the second lead port and the lead engaging mechanism is in the closed position.

26. A system for connecting to a percutaneously implantable medical lead comprising:
   the interface of claim 1;
   a test device; and
   a cable configured to connect the interface to the test device such that the test device is in electrical communication with the at least one contact.

27. The system of claim 26 wherein the test device is an external pulse generator.

28. An interface for coupling to a lead, the lead having a terminal connector at the proximal end of the lead, the terminal connector having at least one terminal contact, the interface comprising:
   a housing comprising a lead port, the lead port comprising an aperture in the housing and a channel, the channel extending into the housing from the aperture and having a lead stop inside the housing and at the end of the channel opposite the aperture, wherein the aperture and the channel have a diameter larger than the diameter of the terminal connector;
   a lead engaging mechanism comprising a knob, a cam, and a cam follower, the cam being rotatable by the knob, the cam follower being biased against the cam and being responsive to the cam such that rotating the cam axially-displaces the cam follower between an open position and a closed position;
   at least one contact which moves responsive to the cam follower, wherein the at least one contact is in a position to be in electrical communication with the at least one terminal contact when the cam follower is in the closed position and the terminal connector is in the lead port; and
   a brake which moves responsive to the cam follower, wherein the brake is in a position where it is frictionally coupled with the lead when the cam follower is in the closed position and the terminal connector is in the lead port, and wherein the brake is in a position where it is not frictionally coupled with the lead when the cam follower is in the open position and the terminal connector is in the lead port,
   wherein the distal end of the lead is implanted in tissue at a distal site, and the terminal connector is removably held in the lead port when the brake is frictionally coupled with the lead such that the force required to remove the terminal connector from the lead port is less than the force required to dislodge the lead from the distal site.

29. A method of securing a terminal connector of a lead in an interface, the terminal connector comprising one or more terminal contacts, the interface comprising a housing with a lead port, the method comprising:
   inserting the terminal connector into the lead port;
   rotating a knob, wherein the knob is coupled to a cam;
   rotating the cam, wherein the cam is coupled to a cam follower and rotating the cam axially displaces the cam follower; and
   moving the cam follower into a closed position, wherein the cam follower is coupled to one or more contacts,
   wherein moving the cam follower into a closed position causes the one or more contacts to be positioned in electrical communication with the one or more terminal contacts.

30. The method of claim 29 wherein:
   the cam follower is coupled to a brake; and
   moving the cam follower into a closed position causes the brake to be in frictional coupling with the lead.

31. The method of claim 29 wherein moving the cam follower into a closed position further comprises biasing a first indexing pin into a position corresponding to the closed position using a first detent.

32. The method of claim 31 wherein rotating the knob comprises overcoming the bias of a second detent on a second indexing pin.

33. The method of claim 29 wherein:
the lead port comprises an aperture in the housing, a channel, and a lead stop at the end of the channel opposite the aperture;
the lead further comprises a stylet or stiffening wire protruding from the terminal connector, the stylet or stiffening wire having an exposed length, the exposed length being the portion of the stylet or stiffening wire between the proximal end of the stylet or stiffening wire and the terminal connector;
the housing further comprises a slot, the slot having a width less that the diameter of the terminal connector but greater than the diameter of the stylet or stiffening wire, the slot extending laterally from the channel to the outside of the housing, the slot extending longitudinally from the aperture, along the length of the channel up to the lead stop, and beyond the lead stop to the side of the housing opposite the aperture; and
inserting the terminal connector into the lead port further comprises passing the exposed length of the stylet or stiffening wire through the slot.

34. The method of claim 29 wherein:
the lead further comprises a retention sleeve;
the lead port further comprises an alignment window extending from the outer surface of the housing to the channel; and
the method further comprising verifying that the retention sleeve is aligned with the alignment window.

35. An interface for coupling to a lead, the lead having a terminal connector at the proximal end of the lead, the terminal connector having at least one terminal contact, the interface comprising:
a housing, the housing comprising a lead port, wherein the lead port is configured to receive the terminal connector;
a lead engaging mechanism, the lead engaging mechanism being variable between an open position and a closed position; and
at least one contact which moves responsive to the lead engaging mechanism, wherein the at least one contact is in a position to be in electrical communication with the at least one terminal contact when the lead engaging mechanism is in the closed position and the terminal connector is in the lead port,
wherein the lead engaging mechanism comprises:
a first detent, wherein the first detent is configured to bias the lead engaging mechanism into the closed position a knob;
a cam, the cam being rotatable by the knob;
a cam follower, the cam follower being biased against the cam, the cam follower being responsive to the cam such that rotating the cam axially-displaces the cam follower between the open position and the closed position; and
a first indexing pin, wherein
the first indexing pin moves responsive to rotation of the knob;
the housing has a first indexing opening;
the first indexing pin extends into the first indexing opening;
the first indexing opening is configured such that the first indexing pin moves along the length of the first indexing opening as it moves responsive to rotation of the knob; and
the first detent biases the first indexing pin into a position in the first indexing opening corresponding to the closed position for the lead engaging mechanism, and
wherein the at least one contact is coupled to the cam follower and moves responsive to the motion of the cam follower.

36. The interface of claim 35 wherein the lead engaging mechanism further comprises a second indexing pin, and wherein:
the second indexing pin moves responsive to rotation of the knob;
the housing has a second indexing opening;
the second indexing opening is configured such that the second indexing pin moves along the length of the second indexing opening as it moves responsive to rotation of the knob; and
the second indexing opening has a detent which biases the second indexing pin into a position in the second indexing opening corresponding to the open position for the lead engaging mechanism.

37. The interface of claim 35 wherein the first indexing opening has a second detent, the second detent biases the first indexing pin into the position corresponding to the open position for the lead engaging mechanism, and the first detent biases the first indexing pin into the position corresponding to the closed position for the lead engaging mechanism.

* * * * *